United States Patent
Bazan

(10) Patent No.: US 6,495,667 B1
(45) Date of Patent: Dec. 17, 2002

(54) IL-B30 ANTIBODIES

(75) Inventor: J. Fernando Bazan, Menlo Park, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/558,087

(22) Filed: Apr. 25, 2000

Related U.S. Application Data

(62) Division of application No. 09/122,443, filed on Jul. 24, 1998, now Pat. No. 6,060,284.
(60) Provisional application No. 60/053,765, filed on Jul. 25, 1997.

(51) Int. Cl.$^7$ .......................... C07K 16/00; G01N 33/53
(52) U.S. Cl. .................. 530/389.2; 530/387.1; 530/387.9; 530/389.1; 435/7.1
(58) Field of Search ............................ 530/387.1, 387.9, 530/389.1, 389.2, 391.1; 435/7.1

(56) References Cited

U.S. PATENT DOCUMENTS 6,060,284 A * 5/2000 Bazan .................. 435/252.3

OTHER PUBLICATIONS

Ngo et al., 1994, The Protein Folding Problem and Tertiary Structure Prediction, pp. 492–495.*
Wells, Aditivity of Mutational Effects in Proteins, 1990, Biochemistry, vol. 26, No.: 37, pp. 8509–8517.*
F.R. Blattner, et al., *GenPept*, Accession No. 2506659, Nov. 1, 1997. Definition: "Hypothetical 55.1 KD Protein In OGT–DBPA Intergenic Region".
T.D. Gaffney, et al., *GenPept*, Accession No. 1172467, Nov. 1, 1995. Definition: "CDP–Diacyglycerol–Glycerol–3–Phosphate 3–Phosphatidylitransferase (Phosphatidylglycerophosphate Synthase) PGP Synthase)."
Toshio Hirano, *The Cytokine Handbook*, Angus W. Thompson, Editor, $2^{nd}$Ed., Ch. 8:145–168, Academic Press, San Diego, 1994, "Interleukin–6".
L. Hillier, et al., *GenBank*, Accession No. AA418955, Oct. 16, 1997. Definition: "zw01c10.r1 Soares NhHMPu S1 Homo sapiens cDNA clone 768018 5'."
Y. Ito, *GenBank*Accession No. AB004061, June 2, 1997. Definition: "domestic pig mRNA for STAT2, complete dcs."
Shigekazu Nagata, *The Cytokine Handbook* Angus W. Thompson, Editor, $2^{nd}$Ed., Ch. 20:371–385–168, Academic Press, San Diego, 1994. "Granulocyte Colony Stimulating Factor and its Receptor."
W. Northemann, et al., *GenPept*, Accession No. 111880, Jun. 18, 1993. Definition: "interleukin–6 precursor—rat."
W. Northemann, et al., *GenPept*, Accession No. 124350, Jul. 15, 1998. Definition: "Interleukin–6 Precursor (IL–6)".
J. Takeda, *GenBank*, Accession No. C06368, Oct. 11, 1996. Definition: "similar to none".
M. Tsuchiya, et al., *GenPept*, Accession No. 117565, Jul. 15, 1998. Definition: "Granulocyte Colony–Stimulating Factor Precursor (G–CSF)."
M. Tsuchiya, et al., *GenPept*, Accession No. 90543, Jun. 7, 1996. Definition: "granulocyte colony–stimulating factor precursor—mouse."
J. Van Snick, et al., *GenPept*, Accession No. 124348, Jul. 15, 1998. Definition: "Interleukin–6 Precursor (IL–6) (Interleukin HP–1 (B–Cell Hybridoma Growth Factor)."
J. Van Snick, et al., *GenPept*, Accession No. 69691, Jun. 7, 1996. Definition: "interleukin–6 precursor—mouse."

* cited by examiner

*Primary Examiner*—Jeffrey Stucker
*Assistant Examiner*—Jegatheesan Sgharaseyon
(74) *Attorney, Agent, or Firm*—Edwin P. Ching; Hugh Wang; Sheela Mohan-Peterson

(57) ABSTRACT

Purified genes encoding cytokine from a mammal, reagents related thereto including purified proteins, specific antibodies, and nucleic acids encoding this molecule are provided. Methods of using said reagents and diagnostic kits are also provided.

8 Claims, No Drawings

IL-B30 ANTIBODIES

This application is a divisional of and claims the benefit of U.S. application Ser. No. 09/122,443 filed Jul. 24, 1998, now U.S. Pat. No. 6,060,284, which claimed priority of provisional Application No. 60/053,765 filed Jul. 25, 1997, now abandoned, the disclosures of which are incorporated by reference.

FIELD OF THE INVENTION

The present invention pertains to compositions related to proteins which function in controlling biology and physiology of mammalian cells, e.g., cells of a mammalian immune system. In particular, it provides purified genes, proteins, antibodies, and related reagents useful, e.g., to regulate activation, development, differentiation, and function of various cell types, including hematopoietic cells.

BACKGROUND OF THE INVENTION

Recombinant DNA technology refers generally to the technique of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host.

For some time, it has been known that the mammalian immune response is based on a series of complex cellular interactions, called the "immune network". Recent research has provided new insights into the inner workings of this network. While it remains clear that much of the response does, in fact, revolve around the network-like interactions of lymphocytes, macrophages, granulocytes, and other cells, immunologists now generally hold the opinion that soluble proteins, known as lymphokines, cytokines, or monokines, play a critical role in controlling these cellular interactions. Thus, there is considerable interest in the isolation, characterization, and mechanisms of action of cell modulatory factors, an understanding of which will lead to significant advancements in the diagnosis and therapy of numerous medical abnormalities, e.g., immune system disorders. Some of these factors are hematopoietic growth factors, e.g., granulocyte colony stimulating factor (G-CSF). See, e.g., Thomson (1994; ed.) *The Cytokine Handbook* (2d ed.) Academic Press, San Diego; Metcalf and Nicola (1995) *The Hematopoietic Colony Stimulating Factors* Cambridge University Press; and Aggarwal and Gutterman (1991) *Human Cytokines* Blackwell Pub.

Lymphokines apparently mediate cellular activities in a variety of ways. They have been shown to support the proliferation, growth, and differentiation of pluripotential hematopoietic stem cells into vast numbers of progenitors comprising diverse cellular lineages making up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types.

Another important cell lineage is the mast cell (which has not been positively identified in all mammalian species), which is a granule-containing connective tissue cell located proximal to capillaries throughout the body. These cells are found in especially high concentrations in the lungs, skin, and gastrointestinal and genitourinary tracts. Mast cells play a central role in allergy-related disorders, particularly anaphylaxis as follows: when selected antigens crosslink one class of immunoglobulins bound to receptors on the mast cell surface, the mast cell degranulates and releases mediators, e.g., histamine, serotonin, heparin, and prostaglandins, which cause allergic reactions, e.g., anaphylaxis.

Research to better understand and treat various immune disorders has been hampered by the general inability to maintain cells of the immune system in vitro. Immunologists have discovered that culturing these cells can be accomplished through the use of T-cell and other cell supernatants, which contain various growth factors, including many of the lymphokines.

From the foregoing, it is evident that the discovery and development of new lymphokines, e.g., related to G-CSF and/or IL-6, could contribute to new therapies for a wide range of degenerative or abnormal conditions which directly or indirectly involve the immune system and/or hematopoietic cells. In particular, the discovery and development of lymphokines which enhance or potentiate the beneficial activities of known lymphokines would be highly advantageous. The present invention provides new interleukin compositions and related compounds, and methods for their use.

SUMMARY OF THE INVENTION

The present invention is directed to mammalian, e.g., rodent, canine, feline, primate, interleukin-B30 (IL-B30) and its biological activities. It includes nucleic acids coding for polypeptides themselves and methods for their production and use. The nucleic acids of the invention are characterized, in part, by their homology to cloned complementary DNA (cDNA) sequences enclosed herein, and/or by functional assays for growth factor- or cytokine-like activities, e.g., G-CSF (see Nagata (1994) in Thomson *The Cytokine Handbook* 2d ed., Academic Press, San Diego) and/or IL-6 (see Hirano (1994) in Thomson *The Cytokine Handbook* 2d ed., Academic Press, San Diego), applied to the polypeptides, which are typically encoded by these nucleic acids. Methods for modulating or intervening in the control of a growth factor dependent physiology or an immune response are provided.

The present invention is based, in part, upon the discovery of a new cytokine sequence exhibiting significant sequence and structural similarity to G-CSF and IL-6. In particular, it provides primate, e.g., human, gene encoding a protein whose mature size is about 168 amino acids, and pig and murine, e.g., mouse, sequences. Functional equivalents exhibiting significant sequence homology will be available from other mammalian, e.g., cow, horse, and rat, and non-mammalian species.

In various protein embodiments, the invention provides: a substantially pure or recombinant IL-B30 protein or peptide exhibiting at least about 85% sequence identity over a length of at least about 12 amino acids to SEQ ID NO: 2; a natural sequence IL-B30 of SEQ ID NO: 2; and a fusion protein comprising IL-B30 sequence. In certain embodiments, the homology is at least about 90% identity and the portion is at least about 9 amino acids; the homology is at least about 80% identity and the portion is at least about 17 amino acids; or the homology is at least about 70% identity and the portion is at least about 25 amino acids. In other embodiments, the IL-B30: comprises a mature sequence of Table 1; or exhibits a post-translational modification pattern distinct from natural IL-B30; or the protein or peptide: is from a warm blooded animal selected from a mammal, including a primate; comprises at least one polypeptide segment of SEQ ID NO: 2; exhibits a plurality of portions exhibiting the identity; is a natural allelic variant of IL-B30; has a length at least about 30 amino acids; exhibits at least two non-overlapping epitopes which are specific for a mammalian IL-B30; exhibits a sequence identity at least about 90% over a length of at least about 20 amino acids to mammalian IL-B30; is glycosylated; has a molecular weight of at least 10 kD with natural glycosylation; is a synthetic polypeptide; is attached to a solid substrate; is conjugated to another chemical moiety; is a 5-fold or less substitution from natural sequence; or is a deletion or insertion variant from a natural sequence. Preferred embodiments include a composition comprising: a sterile IL-B30 protein or peptide; or the IL-B30 protein or peptide and a carrier, wherein the carrier is: an aqueous compound, including water, saline, and/or buffer; and/or formulated for oral, rectal, nasal, topical, or parenteral administration. In fusion protein embodiments, the protein can have: mature protein sequence of Table 1; a detection or purification tag, including a FLAG, His6, or Ig sequence; and/or sequence of another cytokine or chemokine.

Kit embodiments include those with an IL-B30 protein or polypeptide, and: a compartment comprising the protein or polypeptide; and/or instructions for use or disposal of reagents in the kit.

In binding compound embodiments, the compound may have an antigen binding site from an antibody, which specifically binds to a natural IL-B30 protein, wherein: the IL-B30 is a mammalian protein; the binding compound is an Fv, Fab, or Fab2 fragment; the binding compound is conjugated to another chemical moiety; or the antibody: is raised against a peptide sequence of a mature polypeptide of Table 1; is raised against a mature IL-B30; is raised to a purified rodent IL-B30; is immunoselected; is a polyclonal antibody; binds to a denatured IL-B30; exhibits a Kd of at least 30 $\mu$M; is attached to a solid substrate, including a bead or plastic membrane; is in a sterile composition; or is detectably labeled, including a radioactive or fluorescent label. Kits containing binding compounds include those with: a compartment comprising the binding compound; and/or instructions for use or disposal of reagents in the kit. Often the kit is capable of making a qualitative or quantitative analysis. Preferred compositions will comprise: a sterile binding compound; or the binding compound and a carrier, wherein the carrier is: an aqueous compound, including water, saline, and/or buffer; and/or formulated for oral, rectal, nasal, topical, or parenteral administration.

Nucleic acid embodiments include an isolated or recombinant nucleic acid encoding an IL-B30 protein or peptide or fusion protein, wherein: the IL-B30 is from a mammal; and/or the nucleic acid: encodes an antigenic peptide sequence of Table 1; encodes a plurality of antigenic peptide sequences of Table 1; exhibits at least about 80% identity to a natural cDNA encoding the segment; is an expression vector; further comprises an origin of replication; is from a natural source; comprises a detectable label; comprises synthetic nucleotide sequence; is less than 6 kb, preferably less than 3 kb; is from a mammal, including a primate; comprises a natural full length coding sequence; is a hybridization probe for a gene encoding the IL-B30; or is a PCR primer, PCR product, or mutagenesis primer. The invention also provides a cell, tissue, or organ comprising such a recombinant nucleic acid, and preferably the cell will be: a prokaryotic cell; a eukaryotic cell; a bacterial cell; a yeast cell; an insect cell; a mammalian cell; a mouse cell; a primate cell; or a human cell.

Kit embodiments include those with such nucleic acids, and: a compartment comprising the nucleic acid; a compartment further comprising the IL-B30 protein or polypeptide; and/or instructions for use or disposal of reagents in the kit. Typically, the kit is capable of making a qualitative or quantitative analysis.

In certain embodiments, the nucleic acid: hybridizes under wash conditions of 30° C. and less than 2M salt, or of 45° C. and/or 500 mM salt, or 55° C. and/or 150 mM salt, to SEQ ID NO: 1; or exhibits at least about 85% identity and/or the stretch is at least about 30 nucleotides, or exhibits at least 90% identity and/or the stretch is at least 55 nucleotides, or exhibits at least 95% and/or the stretch is at least 75 nucleotides, to a primate IL-B30.

The invention embraces a method of modulating physiology or development of a cell or tissue culture cells comprising contacting the cell with an agonist or antagonist of a mammalian IL-B30. The method may be where: the contacting is in combination with an agonist or antagonist of G-CSF and/or IL-6; or the contacting is with an antagonist, including a binding composition comprising an antibody binding site which specifically binds an IL-B30.

DETAILED DESCRIPTION OF THE
PREFERRED EMBODIMENTS

All references cited herein are incorporated herein by reference to the same extent as if each individual publication or patent application was specifically and individually indicated to be incorporated by reference.

OUTLINE
I. General
II. Purified IL-B30
  A. physical properties
  B. biological properties
III. Physical Variants
  A. sequence variants, fragments
  B. post-translational variants
    1. glycosylation
    2. others
IV. Functional Variants
  A. analogs, fragments
    1. agonists
    2. antagonists
  B. mimetics
    1. protein
    2. chemicals
  C. species variants
V. Antibodies
  A. polyclonal
  B. monoclonal
  C. fragments, binding compositions
VI. Nucleic Acids A. natural isolates; methods
B. synthetic genes
C. methods to isolate VII. Making IL-B30, mimetics
A. recombinant methods
B. synthetic methods
C. natural purification VIII. Uses
A. diagnostic
B. therapeutic IX. Kits
A. nucleic acid reagents
B. protein reagents
C. antibody reagents X. Isolating receptors for IL-B30

I. General

The present invention provides amino acid sequences and DNA sequences encoding various mammalian proteins which are cytokines, e.g., which are secreted molecules which can mediate a signal between immune or other cells. See, e.g., Paul (1994) *Fundamental Immunology* (3d ed.) Raven Press, N.Y. The full length cytokines, and fragments, or antagonists will be useful in physiological modulation of cells expressing a receptor. It is likely that IL-B30 has either stimulatory or inhibitory effects on hematopoietic cells, including, e.g., lymphoid cells, such as T-cells, B-cells, natural killer (NK) cells, macrophages, dendritic cells, hematopoietic progenitors, etc. The proteins will also be useful as antigens, e.g., immunogens, for raising antibodies to various epitopes on the protein, both linear and conformational epitopes.

A cDNA encoding IL-B30 was identified from a human cell line. The molecule was designated huIL-B30. A related gene corresponding to a pig sequence was also identified. A rodent sequence, e.g., from mouse, is also described.

The human gene encodes a small soluble cytokine-like protein, of about 168 amino acids. The signal sequence probably is about 21 residues, and would run from the Met to about Ala. See Table 1 and SEQ. ID. NO: 1 and 2. IL-B30 exhibits structural motifs characteristic of a member of the long chain cytokines. Compare, e.g., IL-B30, G-CSF, and IL-6, sequences available from GenBank. See also Table 2.

TABLE 1

Nucleic acid (SEQ ID NO: 1) encoding IL-B30 from a primate, e.g., human.
Translated amino acid sequence is SEQ ID NO: 2.

```
ATG CTG GGG AGC AGA GCT GTA ATG CTG CTG TTG CTG CTG CCC TGG ACA              48
Met Leu Gly Ser Arg Ala Val Met Leu Leu Leu Leu Leu Pro Trp Thr
-21 -20              -15              -10

GCT CAG GGC AGA GCT GTG CCT GGG GGC AGC AGC CCT GCC TGG ACT CAG              96
Ala Gln Gly Arg Ala Val Pro Gly Gly Ser Ser Pro Ala Trp Thr Gln
-5              1              5              10

TGC CAG CAG CTT TCA CAG AAG CTC TGC ACA CTG GCC TGG AGT GCA CAT             144
Cys Gln Gln Leu Ser Gln Lys Leu Cys Thr Leu Ala Trp Ser Ala His
              15              20              25

CCA CTA GTG GGA CAC ATG GAT CTA AGA GAA GAG GGA GAT GAA GAG ACT             192
Pro Leu Val Gly His Met Asp Leu Arg Glu Glu Gly Asp Glu Glu Thr
              30              35              40

ACA AAT GAT GTT CCC CAT ATC CAG TGT GGA GAT GGC TGT GAC CCC CAA             240
Thr Asn Asp Val Pro His Ile Gln Cys Gly Asp Gly Cys Asp Pro Gln
              45              50              55

GGA CTC AGG GAC AAC AGT CAG TTC TGC TTG CAA AGG ATC CAC CAG GGT             288
Gly Leu Arg Asp Asn Ser Gln Phe Cys Leu Gln Arg Ile His Gln Gly
60              65              70              75

CTG ATT TTT TAT GAG AAG CTG CTA GGA TCG GAT ATT TTC ACA GGG GAG             336
Leu Ile Phe Tyr Glu Lys Leu Leu Gly Ser Asp Ile Phe Thr Gly Glu
              80              85              90

CCT TCT CTG CTC CCT GAT AGC CCT GTG GCG CAG CTT CAT GCC TCC CTA             384
Pro Ser Leu Leu Pro Asp Ser Pro Val Ala Gln Leu His Ala Ser Leu
              95              100              105

CTG GGC CTC AGC CAA CTC CTG CAG CCT GAG GGT CAC CAC TGG GAG ACT             432
Leu Gly Leu Ser Gln Leu Leu Gln Pro Glu Gly His His Trp Glu Thr
              110              115              120

CAG CAG ATT CCA AGC CTC AGT CCC AGC CAG CCA TGG CAG CGT CTC CTT             480
Gln Gln Ile Pro Ser Leu Ser Pro Ser Gln Pro Trp Gln Arg Leu Leu
              125              130              135

CTC CGC TTC AAA ATC CTT CGC AGC CTC CAG GCC TTT GTG GCT GTA GCC             528
Leu Arg Phe Lys Ile Leu Arg Ser Leu Gln Ala Phe Val Ala Val Ala
140              145              150              155

GCC CGG GTC TTT GCC CAT GGA GCA GCA ACC CTG AGT CCC TAA                     570
Ala Arg Val Phe Ala His Gly Ala Ala Thr Leu Ser Pro
              160              165
```

TABLE 1-continued

Nucleic acid (SEQ ID NO: 1) encoding IL-B30 from a primate, e.g., human.
Translated amino acid sequence is SEQ ID NO: 2.

coding sequence:
ATGCTGGGGA GCAGAGCTGT AATGCTGCTG TTGCTGCTGC CCTGGACAGC
TCAGGGCAGA GCTGTGCCTG GGGGCAGCAG CCCTGCCTGG ACTCAGTGCC
AGCAGCTTTC ACAGAAGCTC TGCACACTGG CCTGGAGTGC ACATCCACTA
GTGGGACACA TGGATCTAAG AGAAGAGGGA GATGAAGAGA CTACAAATGA
TGTTCCCCAT ATCCAGTGTG GAGATGGCTG TGACCCCCAA GGACTCAGGG
ACAACAGTCA GTTCTGCTTG CAAAGGATCC ACCAGGGTCT GATTTTTTAT
GAGAAGCTGC TAGGATCGGA TATTTTCACA GGGGAGCCTT CTCTGCTCCC
TGATAGCCCT GTGGCGCAGC TTCATGCCTC CCTACTGGGC CTCAGCCAAC
TCCTGCAGCC TGAGGGTCAC CACTGGGAGA CTCAGCAGAT TCCAAGCCTC
AGTCCCAGCC AGCCATGGCA GCGTCTCCTT CTCCGCTTCA AAATCCTTCG
CAGCCTCCAG GCCTTTGTGG CTGTAGCCGC CCGGGTCTTT GCCCATGGAG
CAGCAACCCT GAGTCCCTAA Rodent, e.g., mouse, IL-B30 (SEQ ID NO: 3 and 4):

```
CGCTTAGAAG TCGGACTACA GAGTTAGACT CAGAACCAAA GGAGGTGGAT AGGGGGTCCA        60

CAGGCCTGGT GCAGATCACA GAGCCAGCCA GATCTGAGAA GCAGGGAACA AG ATG          115
                                                         Met
                                                         -21

CTG GAT TGC AGA GCA GTA ATA ATG CTA TGG CTG TTG CCC TGG GTC ACT        163
Leu Asp Cys Arg Ala Val Ile Met Leu Trp Leu Leu Pro Trp Val Thr
-20             -15                 -10                 -5

CAG GGC CTG GCT GTG CCT AGG AGT AGC AGT CCT GAC TGG GCT CAG TGC        211
Gln Gly Leu Ala Val Pro Arg Ser Ser Ser Pro Asp Trp Ala Gln Cys
                1               5                   10

CAG CAG CTC TCT CGG AAT CTC TGC ATG CTA GCC TGG AAC GCA CAT GCA        259
Gln Gln Leu Ser Arg Asn Leu Cys Met Leu Ala Trp Asn Ala His Ala
        15                  20                  25

CCA GCG GGA CAT ATG AAT CTA CTA AGA GAA GAA GAG GAT GAA GAG ACT        307
Pro Ala Gly His Met Asn Leu Leu Arg Glu Glu Glu Asp Glu Glu Thr
    30                  35                  40

AAA AAT AAT GTG CCC CGT ATC CAG TGT GAA GAT GGT TGT GAC CCA CAA        355
Lys Asn Asn Val Pro Arg Ile Gln Cys Glu Asp Gly Cys Asp Pro Gln
45                  50                  55                  60

GGA CTC AAG GAC AAC AGC CAG TTC TGC TTG CAA AGG ATC CGC CAA GGT        403
Gly Leu Lys Asp Asn Ser Gln Phe Cys Leu Gln Arg Ile Arg Gln Gly
                65                  70                  75

CTG GCT TTT TAT AAG CAC CTG CTT GAC TCT GAC ATC TTC AAA GGG GAG        451
Leu Ala Phe Tyr Lys His Leu Leu Asp Ser Asp Ile Phe Lys Gly Glu
            80                  85                  90

CCT GCT CTA CTC CCT GAT AGC CCC ATG GAG CAA CTT CAC ACC TCC CTA        499
Pro Ala Leu Leu Pro Asp Ser Pro Met Glu Gln Leu His Thr Ser Leu
        95                  100                 105

CTA GGA CTC AGC CAA CTC CTC CAG CCA GAG GAT CAC CCC CGG GAG ACC        547
Leu Gly Leu Ser Gln Leu Leu Gln Pro Glu Asp His Pro Arg Glu Thr
    110                 115                 120

CAA CAG ATG CCC AGC CTG AGT TCT AGT CAG CAG TGG CAG CGC CCC CTT        595
Gln Gln Met Pro Ser Leu Ser Ser Ser Gln Gln Trp Gln Arg Pro Leu
125                 130                 135                 140

CTC CGT TCC AAG ATC CTT CGA AGC CTC CAG GCC TTT TTG GCC ATA GCT        643
Leu Arg Ser Lys Ile Leu Arg Ser Leu Gln Ala Phe Leu Ala Ile Ala
                145                 150                 155

GCC CGG GTC TTT GCC CAC GGA GCA GCA ACT CTG ACT GAG CCC TTA GTG        691
Ala Arg Val Phe Ala His Gly Ala Ala Thr Leu Thr Glu Pro Leu Val
            160                 165                 170

CCA ACA GCT TAAGGATGCC CAGGTTCCCA TGGCTACCAT GATAAGACTA                740
Pro Thr Ala
        175

ATCTATCAGC CCAGACATCT ACCAGTTAAT TAACCCATTA GGACTTGTGC TGTTCTTGTT      800
```

TABLE 1-continued

Nucleic acid (SEQ ID NO: 1) encoding IL-B30 from a primate, e.g., human.
Translated amino acid sequence is SEQ ID NO: 2.

| | | | | | |
|---|---|---|---|---|---:|
| TCGTTTGTTT | TGCGTGAAGG | GCAAGGACAC | CATTATTAAA | GAGAAAAGAA | ACAAACCCCA | 860 |
| GAGCAGGCAG | CTGGCTAGAG | AAAGGAGCTG | GAGAAGAAGA | ATAAAGTCTC | GAGCCCCTTG | 920 |
| CCTTGGAAGC | GGGCAAGCAG | CTGCGTGGCC | TGAGGGGAAG | GGGGCGGTGG | CATCGAGAAA | 980 |
| CTGTGAGAAA | ACCCAGAGCA | TCAGAAAAAG | TGAGCCCAGG | CTTTGGCCAT | TATCTGTAAG | 1040 |
| AAAAACAAGA | AAAGGGGAAC | ATTATACTTT | CCTGGGTGGC | TCAGGGAAAT | GTGCAGATGC | 1100 |
| ACAGTACTCC | AGACAGCAGC | TCTGTACCTG | CCTGCTCTGT | CCCTCAGTTC | TAACAGAATC | 1160 |
| TAGTCACTAA | GAACTAACAG | GACTACCAAT | ACGAACTGAC | AAA | | 1203 |

MLDCRAVIMLWLLPWVTQGLAVPRSSSPDWAQCQQLSRNLCMLAWNAHAPAGHMNLLREEEDEETKNNV
PRIQCEDGCDPQGLKDNSQFCLQRIRQGLAFYKHLLDSDIFKGEPALLPDSPMEQLHTSLLGLSQLLQP
EDHPRETQQMPSLSSSQQWQRPLLRSKILRSLQAFLAIAARVFAHGAATLTEPLVPTA

TABLE 2

Comparison of various IL-6 and G-CSF embodiments compared to
IL-B30. Human IL-B30 is SEQ ID NO: 2; mouse IL-B30 is SEQ ID
NO:4; pig IL-B30 is SEQ ID NO: 5; bovine G-CSF is SEQ ID NO: 6;
feline G-CSF is SEQ ID NO: 7; human G-CSF is SEQ ID NO: 8; mouse
G-CSF is SEQ ID NO: 9; otter IL-6 is SEQ ID NO: 10; feline IL-6
is SEQ ID NO: 11; human IL-6 is SEQ ID NO: 12; sheep IL-6 is
SEQ ID NO: 13; mouse IL-6 is SEQ ID NO: 14; chicken MGF is
SEQ ID NO: 15; and KSHV, kaposi's sarcoma herpes virus, a viral
IL-6, is SEQ ID NO: 16.

```
il30_human     ................VPGG SSPVWTQCQQ LSQKLCT.LA WSAHPLVG..
il30_mouse     ................VPRS SSPDWAQCQQ LSRNLCM.LA WNAHAPAG..
il30_pig       .......... .......... .......... .......... ..........
gcsf_bovin     .......TPLG P.......AR SLPQSFLLKC LEQVRKIQAD GAELQERL..
gcsf_felca     .......TPLG P.......TS SLPQSFLLKC LEQVRKVQAD GTALQERL..
gcsf_human     .......TPLG P.......AS SLPQSFLLKC LEQVRKIQGD GAALQEKLVS
gcsf_mouse     VPLVTVSALP P.......SL PLPRSFLLKS LEQVRKIQAS GSVLLEQL..
il6_otter      .AFPTPGPLG GDSKDDATSN RPPLTSADKM EDFIKFILGK ISALRNEM..
il6_felca      .AFPTPGPLG G....DATSN RLPLTPADKM EELIKYILGK ISALKKEM..
il6_human      .AFPAPVPPG EDSKDVAAPH RQPLTSSERI DKQIRYILDG ISALRKET..
il6_sheep      .AFPTPGPLG EDFKNDTTPS RLLLTTPEKT EALIKHIVDK ISAIRKEI..
il6_mouse      .AFPTSQVRR GDFTEDTTPN R.PVYTTSQV GGLITHVLWE IVEMRKEL..
mgf_chick      .......... .APLAELSGD HDFQLFLHKN LEFTRKIRGD VAALQRAV..
il6_khsv       .......... .......TRG KLPDAPEFEK DLLIQRLNWM LWVIDECFRD il30_human     .HMD.LREEG DEETTNDVPH I...QCGDGC DPQGLRDNSQ FCLQRIHQGL
il30_mouse     .HMNLLREEE DEETKNNVPR I...QCEDGC DPQGLKDNSQ FCLQRIRQGL
il30_pig       .......... .......... .......... .......... SCLQRIHQGL
gcsf_bovin     .CAA.HKLCH PEELMLLRHS LGIP.QAPLS SCSSQSLQLR GCLNQLHGGL
gcsf_felca     .CAA.HKLCH PEELVLLGHA LGIP.QAPLS SCSSQALQLT GCLRQLHSGL
gcsf_human     ECAT.YKLCH PEELVLLGHS LGIP.QAPLS SCPSQALQLA GCLSQLHSGL
gcsf_mouse     .CAT.YKLCH PEELVLLGHS LGIP.KASLS GCSSQALQQT QCLSQLHSGL
il6_otter      .CDK.YNKCE DSKEVLAENN LNLPKLAEKD RCFQSRFNQE TCLTRITTGL
il6_felca      .CDN.YNKCE DSKEALAENN LNLPKLAEKD GCFQSGFNQE TCLTRITTGL
il6_human      .CNK.SNMCE SSKEALAENN LNLPKMAEKD GCFQSGFNEE TCLVKIITGL
il6_sheep      .CEK.NDECE NSKETLAENK LKLPKMEEKD GCFQSGFNQA ICLIKTTAGL
il6_mouse      .CNG.NSDCM NNDDALAENN LKLPEIQRND GCYQTGYNQE ICLLKISSGL
mgf_chick      .CDT.FQLCT EEELQLVQPD PHLV.QAPLD QCHKRGFQAE VCFTQIRAGL
il6_khsv       LCYR.TGICK GILEPAAIFH LKLPAINDTD HCGLIGFNET SCLKKLADGF il30_human     IFYEKLLGSD IFTGE..... .PSLLPDSPV AQLHASLLGL SQLLQPE..G
il30_mouse     AFYKHLLDSD IFKGE..... .PALLPDSPM EQLHTSLLGL SQLLQPE..D
il30_pig       VFYEKLLGSD IFTGE..... .PSLHPDGSV QLHASLLGL RQLLQPE..G
gcsf_bovin     FLYQGLLQAL AGIS...... .PELAPTLDT LQLDVTDFAT NIWLQMEDLG
gcsf_felca     FLYQGLLQAL AGIS...... .PELAPTLDM LQLDITDFAI NIWQQMEDVG
gcsf_human     FLYQGLLQAL EGIS...... .PELGPTLDT LQLDVADFAT TIWQQMEELG
gcsf_mouse     CLYQGLLQAL SGIS...... .PALAPTLDL LQLDVANFAT TIWQQMENLG
il6_otter      QEFQIHLKYL ESNYEG...N KDNAHSVYIS TKHLLQTLRP M..NQIEVTT
il6_felca      QEFQIYLKFL QDKYEG...D KENAKSVYTS TNVLLQMLKR KGKNQDEVTI
il6_human      LEFEVYLEYL QNRFES...S EEQARAVQMS TKVLIQFLQK KAKNLDAITT
il6_sheep      LEYQIYLDFL QNEFEG...N QETVMELQSS IRTLIQILKE KIAGL....I
il6_mouse      LEYHSYLEYM KNNLKDN..K KDKARVLQRD TETLIHIFNQ EVKDLHKIVL
mgf_chick      HAYHDSLGAV LRLLP..... ..NHTTLVET LQLDAANLSS NIQQQMEDLG
```

TABLE 2-continued

Comparison of various IL-6 and G-CSF embodiments compared to IL-B30. Human IL-B30 is SEQ ID NO: 2; mouse IL-B30 is SEQ ID NO:4; pig IL-B30 is SEQ ID NO: 5; bovine G-CSF is SEQ ID NO: 6; feline G-CSF is SEQ ID NO: 7; human G-CSF is SEQ ID NO: 8; mouse G-CSF is SEQ ID NO: 9; otter IL-6 is SEQ ID NO: 10; feline IL-6 is SEQ ID NO: 11; human IL-6 is SEQ ID NO: 12; sheep IL-6 is SEQ ID NO: 13; mouse IL-6 is SEQ ID NO: 14; chicken MGF is SEQ ID NO: 15; and KSHV, kaposi's sarcoma herpes virus, a viral IL-6, is SEQ ID NO: 16.

```
il6_khsv     FEFEVLFKFL TTEFGKSVIN VDVMELLTKT LGWDIQEELN KLTKTHY..S il30_human   HHWETQQIP. .SLSPSQ..P WQRLLLRFKI LRSLQAFVAV AARVFAHGAA
il30_mouse   HPRETQQMP. .SLSSSQ..Q WQRPLLRSKI LRSLQAFLAI AARVFAHGAA
il30_pig     HHWETEQTP. .SPSPSQ..P WQRLLLRLKI LRSLQAFVAV AARVFAHGAA
gcsf_bovin   AAPAVQPTQ. .GAMPTFTSA FQRRAGGVLV ASQLHRFLEL AYRGLRYLAE
gcsf_felca   MAPAVPPTQ. .GTMPTFTSA FQRRAGGTLV ASNLQSFLEV AYRALRHFTK
gcsf_human   MAPALQPTQ. .GAMPAFASA FQRRAGGVLV ASHLQSFLEV SYRVLRHLAQ
gcsf_mouse   VAPTVQPTQ. .SAMPAFTSA FQRRAGGVLA ISYLQGFLET ARLALHHLA.
il6_otter    PDPTTDASL. .QALFKSQDK WLKHTTIHLI LRRLEDFLQF SLRAIRIM..
il6_felca    PVPTVEVGL. .QLSCSHR.R VAEAHNNHLT LRRLEDFLQL RLRAVRIM..
il6_human    PDPTTNASL. .LTKLQAQNQ WLQDMTTHLI LRSFKEFLQS SLRALRQM..
il6_sheep    TTPATHTDM. .LEKMQSSNE WVKNAKVIII LRSLENFLQF SLRAIRMK..
il6_mouse    PTPISNALL. .TDKLESQKE WLRTKTIQFI LKSLEEFLKV TLRSTRQT..
mgf_chick    LDTVTLPAEQ RSPPPTFSGP FQQQVGGFFI LANFQRFLET AYRALRHLAR
il6_khsv     P.PKFDRG.. LLGRLQGLKY WVRHFASFYV LSAMEKFAGQ AVRVLDSIPD il30_human   TLSP....
il30_mouse   TLTEPLVPTA
il30_pig     TLSQ....
gcsf_bovin   P.......
gcsf_felca   P.......
gcsf_human   P.......
gcsf_mouse   ........
il6_otter    ........
il6_felca    ........
il6_human    ........
il6_sheep    ........
il6_mouse    ........
mgf_chick    L.......
il6_khsv     VTPDVHDK
```

The structural homology of IL-B30 to related cytokine proteins suggests related function of this molecule. IL-B30 is a long chain cytokine exhibiting sequence similarity to IL-6 and G-CSF.

IL-B30 agonists, or antagonists, may also act as functional or receptor antagonists, e.g., which block IL-6 or G-CSF binding to their respective receptors, or mediating the opposite actions. Thus, IL-B30, or its antagonists, may be useful in the treatment of abnormal medical conditions, including immune disorders, e.g., T cell immune deficiencies, chronic inflammation, or tissue rejection, or in cardiovascular or neurophysiological conditions.

The natural antigens are capable of mediating various biochemical responses which lead to biological or physiological responses in target cells. The preferred embodiment characterized herein is from human, but other primate, or other species counterparts exist in nature. Additional sequences for proteins in other mammalian species, e.g., primates, canines, felines, and rodents, should also be available. See below. The descriptions below are directed, for exemplary purposes, to a human IL-B30, but are likewise applicable to related embodiments from other species.

II. Purified IL-B30

Human IL-B30 amino acid sequence, is shown as one embodiment within SEQ ID NO: 2. Other naturally occurring nucleic acids which encode the protein can be isolated by standard procedures using the provided sequence, e.g., PCR techniques, or by hybridization. These amino acid sequences, provided amino to carboxy, are important in providing sequence information for the cytokine allowing for distinguishing the protein antigen from other proteins and exemplifying numerous variants. Moreover, the peptide sequences allow preparation of peptides to generate antibodies to recognize such segments, and nucleotide sequences allow preparation of oligonucleotide probes, both of which are strategies for detection or isolation, e.g., cloning, of genes encoding such sequences.

As used herein, the term "human soluble IL-B30" shall encompass, when used in a protein context, a protein having amino acid sequence corresponding to a soluble polypeptide shown in SEQ ID NO: 2, or significant fragments thereof. Preferred embodiments comprise a plurality of distinct, e.g., nonoverlapping, segments of the specified length. Typically, the plurality will be at least two, more usually at least three, and preferably 5, 7, or even more. While the length minima are provided, longer lengths, of various sizes, may be appropriate, e.g., one of length 7, and two of length 12.

Binding components, e.g., antibodies, typically bind to an IL-B30 with high affinity, e.g., at least about 100 nM, usually better than about 30 nM, preferably better than about 10 nM, and more preferably at better than about 3 nM. Counterpart proteins will be found in mammalian species other than human, e.g., other primates, ungulates, or rodents. Nonmammalian species should also possess structurally or functionally related genes and proteins, e.g., birds or amphibians.

The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids, e.g., 35, 40, 45, 50, etc. Such fragments may have ends which begin and/or end at virtually all positions, e.g., beginning at residues 1, 2, 3, etc., and ending at, e.g., 150, 149, 148, etc., in all practical combinations. Particularly interesting peptides have ends corresponding to structural domain boundaries, e.g., helices A, B, C, and/or D. See Table 1.

The term "binding composition" refers to molecules that bind with specificity to IL-B30, e.g., in an antibody-antigen interaction. The specificity may be more or less inclusive, e.g., specific to a particular embodiment, or to groups of related embodiments, e.g., primate, rodent, etc. It also includes compounds, e.g., proteins, which specifically associate with IL-B30, including in a natural physiologically relevant protein-protein interaction, either covalent or non-covalent. The molecule may be a polymer, or chemical reagent. A functional analog may be a protein with structural modifications, or it may be a molecule which has a molecular shape which interacts with the appropriate binding determinants. The compounds may serve as agonists or antagonists of a receptor binding interaction, see, e.g., Goodman, et al. (eds.) *Goodman & Gilman's: The Pharmacological Bases of Therapeutics* (current ed.) Pergamon Press.

Substantially pure, e.g., in a protein context, typically means that the protein is free from other contaminating proteins, nucleic acids, or other biologicals derived from the original source organism. Purity may be assayed by standard methods, typically by weight, and will ordinarily be at least about 40% pure, generally at least about 50% pure, often at least about 60% pure, typically at least about 80% pure, preferably at least about 90% pure, and in most preferred embodiments, at least about 95% pure. Carriers or excipients will often be added.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. For diagnostic purposes, the temperature will usually be about room temperature or warmer, but less than the denaturation temperature of components in the assay. For therapeutic purposes, the temperature will usually be body temperature, typically about 37° C. for humans and mice, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents.

The solvent and electrolytes will usually be a biologically compatible buffer, of a type used for preservation of biological activities, and will usually approximate a physiological aqueous solvent. Usually the solvent will have a neutral pH, typically between about 5 and 10, and preferably about 7.5. On some occasions, one or more detergents will be added, typically a mild non-denaturing one, e.g., CHS (cholesteryl hemisuccinate) or CHAPS (3-[3-cholamidopropyl)dimethylammonio]-1-propane sulfonate), or a low enough concentration as to avoid significant disruption of structural or physiological properties of the protein. In other instances, a harsh detergent may be used to effect significant denaturation.

III. Physical Variants

This invention also encompasses proteins or peptides having substantial amino acid sequence identity with the amino acid sequence of the IL-B30 antigen. The variants include species, polymorphic, or allelic variants.

Amino acid sequence homology, or sequence identity, is determined by optimizing residue matches, if necessary, by introducing gaps as required. See also Needleham, et al. (1970) *J. Mol. Biol.* 48:443–453; Sankoff, et al. (1983) Chapter One in *Time Warps, String Edits, and Macromolecules: The Theory and Practice of Sequence Comparison*, Addison-Wesley, Reading, Mass.; and software packages from IntelliGenetics, Mountain View, Calif.; and the University of Wisconsin Genetics Computer Group, Madison, Wis. Sequence identity changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. The conservation may apply to biological features, functional features, or structural features. Homologous amino acid sequences are typically intended to include natural polymorphic or allelic and interspecies variations of a protein sequence. Typical homologous proteins or peptides will have from 25–100% identity (if gaps can be introduced), to 50–100% identity (if conservative substitutions are included) with the amino acid sequence of the IL-B30. Identity measures will be at least about 35%, generally at least about 40%, often at least about 50%, typically at least about 60%, usually at least about 70%, preferably at least about 80%, and more preferably at least about 90%.

The isolated IL-B30 DNA can be readily modified by nucleotide substitutions, nucleotide deletions, nucleotide insertions, and inversions of short nucleotide stretches. These modifications result in novel DNA sequences which encode these antigens, their derivatives, or proteins having similar physiological, immunogenic, antigenic, or other functional activity. These modified sequences can be used to produce mutant antigens or to enhance expression. Enhanced expression may involve gene amplification, increased transcription, increased translation, and other mechanisms. "Mutant IL-B30" encompasses a polypeptide otherwise falling within the sequence identity definition of the IL-B30 as set forth above, but having an amino acid sequence which differs from that of IL-B30 as normally found in nature, whether by way of deletion, substitution, or insertion. This generally includes proteins having significant identity with a protein having sequence of SEQ ID NO: 2, and as sharing various biological activities, e.g., antigenic or immunogenic, with those sequences, and in preferred embodiments contain most of the natural full length disclosed sequences. Full length sequences will typically be preferred, though truncated versions will also be useful, likewise, genes or proteins found from natural sources are typically most desired. Similar concepts apply to different IL-B30 proteins, particularly those found in various warm blooded animals, e.g., mammals and birds. These descriptions are generally meant to encompass all IL-B30 proteins, not limited to the particular primate embodiments specifically discussed.

IL-B30 mutagenesis can also be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See, e.g., Sambrook, et al. (1989); Ausubel, et al. (1987 and Supplements); and Kunkel, et al. (1987) *Methods in Enzymol.* 154:367–382. Preferred embodiments include, e.g., 1-fold, 2-fold, 3-fold, 5-fold, 7-fold, etc., preferably conservative substitutions at the nucleotide or amino acid levels. Preferably the substitutions will be away from the conserved cysteines, and often will be in the regions away from the helical structural domains. Such variants may be useful to produce specific antibodies, and often will share many or all biological properties.

The present invention also provides recombinant proteins, e.g., heterologous fusion proteins using segments from these proteins. A heterologous fusion protein is a fusion of proteins or segments which are naturally not normally fused in the same manner. A similar concept applies to heterologous nucleic acid sequences.

In addition, new constructs may be made from combining similar functional domains from other proteins. For example, target-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

Structural analysis can be applied to this gene, in-comparison to the IL-6 family of cytokines. The family includes, e.g., IL-6, IL-11, IL-12, G-CSF, LIF, OSM, CNTF, and Ob. Alignment of the human, pig, and mouse IL-B30 sequences with other members of the IL-6 family should allow definition of structural features. In particular, β-sheet and α-helix residues can be determined using, e.g., RASMOL program, see Bazan, et al. (1996) *Nature* 379:591; Lodi, et al. (1994) *Science* 263:1762–1766; Sayle and Milner-White (1995) *TIBS* 20:374–376; and Gronenberg, et al. (1991) *Protein Engineering* 4:263–269. Preferred residues for substitutions include the surface exposed residues which would be predicted to interact with receptor. Other residues which should conserve function will be conservative substitutions, particularly at position far from the surface exposed residues.

IV. Functional Variants

The blocking of physiological response to IL-B30s may result from the competitive inhibition of binding of the ligand to its receptor.

In vitro assays of the present invention will often use isolated protein, soluble fragments comprising receptor binding segments of these proteins, or fragments attached to solid phase substrates. These assays will also allow for the diagnostic determination of the effects of either binding segment mutations and modifications, or cytokine mutations and modifications, e.g., IL-B30 analogs.

This invention also contemplates the use of competitive drug screening assays, e.g., where neutralizing antibodies to the cytokine, or receptor binding fragments compete with a test compound.

"Derivatives" of IL-B30 antigens include amino acid sequence mutants from naturally occurring forms, glycosylation variants, and covalent or aggregate conjugates with other chemical moieties. Covalent derivatives can be prepared by linkage of functionalities to groups which are found in IL-B30 amino acid side chains or at the N- or C-termini, e.g., by standard means. See, e.g., Lundblad and Noyes (1988) *Chemical Reagents for Protein Modification*, vols. 1–2, CRC Press, Inc., Boca Raton, Fla.; Hugli (ed. 1989) *Techniques in Protein Chemistry*, Academic Press, San Diego, Calif.; and Wong (1991) *Chemistry of Protein Conjugation and Cross Linking*, CRC Press, Boca Raton, Fla.

In particular, glycosylation alterations are included, e.g., made by modifying the glycosylation patterns of a polypeptide during its synthesis and processing, or in further processing steps. See, e.g., Elbein (1987) *Ann. Rev. Biochem.* 56:497–534. Also embraced are versions of the peptides with the same primary amino acid sequence which have other minor modifications, including phosphorylated amino acid residues, e.g., phosphotyrosine, phosphoserine, or phosphothreonine.

Fusion polypeptides between IL-B30s and other homologous or heterologous proteins are also provided. Many cytokine receptors or other surface proteins are multimeric, e.g., homodimeric entities, and a repeat construct may have various advantages, including lessened susceptibility to proteolytic cleavage. Typical examples are fusions of a reporter polypeptide, e.g., luciferase, with a segment or domain of a protein, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, yeast alpha mating factor, and detection or purification tags such as a FLAG sequence of His6 sequence. See, e.g., Godowski, et al. (1988) *Science* 241:812–816.

Fusion peptides will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), vols. 1–3, Cold Spring Harbor Laboratory; and Ausubel, et al. (eds. 1993) *Current Protocols in Molecular Biology*, Greene and Wiley, N.Y. Techniques for synthesis of polypeptides are described, e.g., in Merrifield (1963) *J. Amer. Chem. Soc.* 85:2149–2156; Merrifield (1986) *Science* 232: 341–347; Atherton, et al. (1989) *Solid Phase Peptide Synthesis: A Practical Approach*, IRL Press, Oxford; and Grant (1992) *Synthetic Peptides: A User's Guide*, W. H. Freeman, N.Y. Refolding methods may be applicable to synthetic proteins.

This invention also contemplates the use of derivatives of IL-B30 proteins other than variations in amino acid sequence or glycosylation. Such derivatives may involve covalent or aggregative association with chemical moieties or protein carriers. Covalent or aggregative derivatives will be useful as immunogens, as reagents in immunoassays, or in purification methods such as for affinity purification of binding partners, e.g., other antigens. An IL-B30 can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-IL-B30 antibodies or an alternative binding composition. The IL-B30 proteins can also be labeled with a detectable group, e.g., for use in diagnostic assays. Purification of IL-B30 may be effected by an immobilized antibody or complementary binding partner, e.g., binding portion of a receptor.

A solubilized IL-B30 or fragment of this invention can be used as an immunogen for the production of antisera or antibodies specific for binding. Purified antigen can be used to screen monoclonal antibodies or antigen-binding fragments, encompassing antigen binding fragments of natural antibodies, e.g., Fab, Fab', F(ab)$_2$, etc. Purified IL-B30 antigens can also be used as a reagent to detect antibodies generated in response to the presence of elevated levels of the cytokine, which may be diagnostic of an abnormal or specific physiological or disease condition. This invention contemplates antibodies raised against amino acid sequences encoded by nucleotide sequence shown in SEQ ID NO: 1, or fragments of proteins containing it. In particular, this invention contemplates antibodies having binding affinity to or being raised against specific domains, e.g., helices A, B, C, or D.

The present invention contemplates the isolation of additional closely related species variants. Southern and Northern blot analysis will establish that similar genetic entities exist in other mammals. It is likely that IL-B30s are widespread in species variants, e.g., rodents, lagomorphs, carnivores, artiodactyla, perissodactyla, and primates.

The invention also provides means to isolate a group of related antigens displaying both distinctness and similarities in structure, expression, and function. Elucidation of many of the physiological effects of the molecules will be greatly accelerated by the isolation and characterization of additional distinct species or polymorphic variants of them. In particular, the present invention provides useful probes for identifying additional homologous genetic entities in different species.

The isolated genes will allow transformation of cells lacking expression of an IL-B30, e.g., either species types or cells which lack corresponding proteins and exhibit negative background activity. This should allow analysis of the function of IL-B30 in comparison to untransformed control cells.

Dissection of critical structural elements which effect the various physiological functions mediated through these antigens is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390.

Intracellular functions would probably involve receptor signaling. However, protein internalization may occur under certain circumstances, and interaction between intracellular components and cytokine may occur. Specific segments of interaction of IL-B30 with interacting components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Further study of the expression and control of IL-B30 will be pursued. The controlling elements associated with the antigens should exhibit differential physiological, developmental, tissue specific, or other expression patterns. Upstream or downstream genetic regions, e.g., control elements, are of interest.

Structural studies of the IL-B30 antigens will lead to design of new antigens, particularly analogs exhibiting agonist or antagonist properties on the molecule. This can be combined with previously described screening methods to isolate antigens exhibiting desired spectra of activities.

V. Antibodies

Antibodies can be raised to various epitopes of the IL-B30 proteins, including species, polymorphic, or allelic variants, and fragments thereof, both in their naturally occurring forms and in their recombinant forms. Additionally, antibodies can be raised to IL-B30s in either their active forms or in their inactive forms, including native or denatured versions. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective IL-B30s, or screened for agonistic or antagonistic activity, e.g., mediated through a receptor. Antibodies may be agonistic or antagonistic, e.g., by sterically blocking binding to a receptor. These monoclonal antibodies will usually bind with at least a $K_D$ of about 1 mM, more usually at least about 300 $\mu$M, typically at least about 100 $\mu$M, more typically at least about 30 $\mu$M, preferably at least about 10 $\mu$M, and more preferably at least about 3 $\mu$M or better.

The antibodies of this invention can also be useful in diagnostic applications. As capture or non-neutralizing antibodies, they can be screened for ability to bind to the antigens without inhibiting binding to a receptor. As neutralizing antibodies, they can be useful in competitive binding assays. They will also be useful in detecting or quantifying IL-B30 protein or its receptors. See, e.g., Chan (ed. 1987) *Immunology: A Practical Guide*, Academic Press, Orlando, Fla.; Price and Newman (eds. 1991) *Principles and Practice of Immunoassay*, Stockton Press, N.Y.; and Ngo (ed. 1988) *Nonisotopic Immunoassay*, Plenum Press, N.Y. Cross absorptions or other tests will identify antibodies which exhibit various spectra of specificities, e.g., unique or shared species specificities.

Further, the antibodies, including antigen binding fragments, of this invention can be potent antagonists that bind to the antigen and inhibit functional binding, e.g., to a receptor which may elicit a biological response. They also can be useful as non-neutralizing antibodies and can be coupled to toxins or radionuclides so that when the antibody binds to antigen, a cell expressing it, e.g., on its surface, is killed. Further, these antibodies can be conjugated to drugs or other therapeutic agents, either directly or indirectly by means of a linker, and may effect drug targeting.

Antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; Williams, et al. (1967) *Methods in Immunology and Immunochemistry*, vol. 1, Academic Press, New York; and Harlow and Lane (1988) *Antibodies: A Laboratory Manual*, CSH Press, N.Y., for descriptions of methods of preparing polyclonal antisera.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.), Academic Press, New York; and particularly in Kohler and Milstein (1975) in *Nature* 256:495–497, which discusses one method of generating monoclonal antibodies.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; Moore, et al., U.S. Pat. No. 4,642,334; and Queen, et al. (1989) *Proc. Nat'l Acad. Sci. USA* 86:10029–10033.

The antibodies of this invention can also be used for affinity chromatography in isolating the protein. Columns can be prepared where the antibodies are linked to a solid support. See, e.g., Wilchek et al. (1984) *Meth. Enzymol.* 104:3–55.

Antibodies raised against each IL-B30 will also be useful to raise anti-idiotypic antibodies. These will be useful in detecting or diagnosing various immunological conditions related to expression of the respective antigens.

VI. Nucleic Acids

The described peptide sequences and the related reagents are useful in detecting, isolating, or identifying a DNA clone encoding IL-B30, e.g., from a natural source. Typically, it will be useful in isolating a gene from mammal, and similar procedures will be applied to isolate genes from other species, e.g., warm blooded animals, such as birds and mammals. Cross hybridization will allow isolation of IL-B30 from the same, e.g., polymorphic variants, or other species. A number of different approaches will be available to successfully isolate a suitable nucleic acid clone.

The purified protein or defined peptides are useful for generating antibodies by standard methods, as described above. Synthetic peptides or purified protein can be presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual*, Cold Spring Harbor Press.

For example, the specific binding composition could be used for screening of an expression library made from a cell line which expresses an IL-B30. Screening of intracellular expression can be performed by various staining or immunofluorescence procedures. Binding compositions could be used to affinity purify or sort out cells expressing a surface fusion protein.

The peptide segments can also be used to predict appropriate oligonucleotides to screen a library. The genetic code can be used to select appropriate oligonucleotides useful as probes for screening. See, e.g., SEQ ID NO: 1. In combination with polymerase chain reaction (PCR) techniques, synthetic oligonucleotides will be useful in selecting correct clones from a library. Complementary sequences will also be used as probes, primers, or antisense strands. Various fragments should be particularly useful, e.g., coupled with anchored vector or poly-A complementary PCR techniques or with complementary DNA of other peptides.

This invention contemplates use of isolated DNA or fragments to encode a biologically active corresponding IL-B30 polypeptide, particularly lacking the portion coding the untranslated 5' portion of the described sequence. In addition, this invention covers isolated or recombinant DNA which encodes a biologically active protein or polypeptide and which is capable of hybridizing under appropriate conditions with the DNA sequences described herein. Said biologically active protein or polypeptide can be an intact antigen, or fragment, and have an amino acid sequence disclosed in, e.g., SEQ ID NO: 2, particularly a mature, secreted polypeptide. Further, this invention covers the use of isolated or recombinant DNA, or fragments thereof, which encode proteins which exhibit high identity to a secreted IL-B30. The isolated DNA can have the respective regulatory sequences in the 5' and 3' flanks, e.g., promoters, enhancers, poly-A addition signals, and others. Alternatively, expression may be effected by operably linking a coding segment to a heterologous promoter, e.g., by inserting a promoter upstream from an endogenous gene. An "isolated" nucleic acid is a nucleic acid, e.g., an RNA, DNA, or a mixed polymer, which is substantially separated from other components which naturally accompany a native sequence, e.g., ribosomes, polymerases, and/or flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Generally, the nucleic acid will be in a vector or fragment less than about 50 kb, usually less than about 30 kb, typically less than about 10 kb, and preferably less than about 6 kb.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, e.g., products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site.

Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species or polymorphic variants.

A significant "fragment" in a nucleic acid context is a contiguous segment of at least about 17 nucleotides, generally at least about 22 nucleotides, ordinarily at least about 29 nucleotides, more often at least about 35 nucleotides, typically at least about 41 nucleotides, usually at least about 47 nucleotides, preferably at least about 55 nucleotides, and in particularly preferred embodiments will be at least about 60 or more nucleotides, e.g., 67, 73, 81, 89, 95, etc.

A DNA which codes for an IL-B30 protein will be particularly useful to identify genes, MRNA, and cDNA species which code for related or similar proteins, as well as DNAs which code for homologous proteins from different species. There will be homologs in other species, including primates, rodents, canines, felines, and birds. Various IL-B30 proteins should be homologous and are encompassed herein. However, even proteins that have a more distant evolutionary relationship to the antigen can readily be isolated under appropriate conditions using these sequences if they are sufficiently homologous. Primate IL-B30 proteins are of particular interest. Recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology*, Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Embryonic Stem Cells: A Practical Approach*, IRL Press, Oxford; and Rosenberg (1992) *J. Clinical Oncology* 10:180–199.

Substantial homology, e.g., identity, in the nucleic acid sequence comparison context means either that the segments, or their complementary strands, when compared, are identical when optimally aligned, with appropriate nucleotide insertions or deletions, in at least about 50% of the nucleotides, generally at least about 58%, ordinarily at least about 65%, often at least about 71%, typically at least about 77%, usually at least about 85%, preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence of IL-B30, e.g., in SEQ ID NO: 1. Typically, selective hybridization will occur when there is at least about 55% identity over a stretch of at least about 30 nucleotides, preferably at least about 75% over a stretch of about 25 nucleotides, and most preferably at least about 90% over about 20 nucleotides. See, Kanehisa (1984) *Nuc. Acids Res.* 12:203–213. The length of identity comparison, as described, may be over longer stretches, and in certain embodiments will be over a stretch of at least about 17 nucleotides, usually at least about 28 nucleotides, typically at least about 40 nucleotides, and preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperatures conditions will usually include temperature in excess of about 30° C., usually in excess of about 37° C., typically in excess of about 55° C., Preferably in excess of about 70° C. Stringent salt conditions will ordinarily be less than about 1000 mM, usually less than about 400 mM, typically less than about 250 mM, preferably less than about 150 mM, including about 100, 50, or even 20 mM. However, the combination of parameters is such more important than the measure of any single parameter. See, e.g., Wetmur and Davidson (1968) *J. Mol. Biol.* 31:349–370. Hybridization under stringent conditions should give a background of at least 2-fold over background, preferably at least 3–5 or more.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng and Doolittle (1987) *J. Mol. Evol.* 35:351–360. The method used is similar to the method described by Higgins and Sharp (1989) *CABIOS* 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul, et al. (1990) *J. Mol. Biol.* 215:403–410. Software for performing BLAST analyses is publicly available through the National Center for Biotechnology Information (http:www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) *Proc. Nat'l Acad. Sci. USA* 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) *Proc. Nat'l Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

IL-B30 from other mammalian species can be cloned and isolated by cross-species hybridization of closely related species. Homology may be relatively low between distantly related species, and thus hybridization of relatively closely related species is advisable. Alternatively, preparation of an antibody preparation which exhibits less species specificity may be useful in expression cloning approaches.

VII. Making IL-B30; Mimetics

DNA which encodes the IL-B30 or fragments thereof can be obtained by chemical synthesis, screening cDNA libraries, or screening genomic libraries prepared from a wide variety of cell lines or tissue samples. See, e.g., Okayama and Berg (1982) *Mol. Cell. Biol.* 2:161–170; Gubler and Hoffman (1983) *Gene* 25:263–269; and Glover (ed. 1984) *DNA Cloning: A Practical Approach*, IRL Press, Oxford. Alternatively, the sequences provided herein provide useful PCR primers or allow synthetic or other preparation of suitable genes encoding an IL-B30; including naturally occurring embodiments.

This DNA can be expressed in a wide variety of host cells for the synthesis of a full-length IL-B30 or fragments which can in turn, e.g., be used to generate polyclonal or monoclonal antibodies; for binding studies; for construction and expression of modified molecules; and for structure/function studies.

Vectors, as used herein, comprise plasmids, viruses, bacteriophage, integratable DNA fragments, and other vehicles which enable the integration of DNA fragments into the genome of the host. See, e.g., Pouwels, et al. (1985 and Supplements) *Cloning Vectors: A Laboratory Manual*, Elsevier, N.Y.; and Rodriguez, et al. (eds. 1988) *Vectors: A Survey of Molecular Cloning Vectors and Their Uses*, Buttersworth, Boston, Mass.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression. See, e.g., Rodriguez, et al., Chapter 10, pp. 205–236; Balbas and Bolivar (1990) *Methods in Enzymology* 185:14–37; and Ausubel, et al. (1993) *Current Protocols in Molecular Biolocry*, Greene and Wiley, N.Y.

Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610. See, e.g., Miller (1988) *Ann. Rev. Microbiol.* 42:177–199.

It will often be desired to express an IL-B30 polypeptide in a system which provides a specific or defined glycosylation pattern. See, e.g., Luckow and Summers (1988) *Bio/Technolocry* 6:47–55; and Kaufman (1990) *Meth. Enzymol.* 185:487–511.

The IL-B30, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biopys. Acta* 988:427–454; Tse, et al. (1985) *Science* 230:1003–1008; and Brunner, et al. (1991) *J. Cell Biol.* 114:1275–1283.

Now that the IL-B30 has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, N.Y.; Bodanszky (1984) *The Principles of Peptide Synthesis*, Springer-Verlag, N.Y.; and Villafranca (ed. 1991) *Techniques in Protein Chemistry II*, Academic Press, San Diego, Calif.

VIII. Uses

The present invention provides reagents which will find use in diagnostic applications as described elsewhere herein, e.g., in IL-B30 mediated conditions, or below in the description of kits for diagnosis. The gene may be useful in forensic sciences, e.g., to distinguish rodent from human, or as a marker to distinguish between different cells exhibiting differential expression or modification patterns.

This invention also provides reagents with significant commercial and/or therapeutic potential. The IL-B30 (naturally occurring or recombinant), fragments thereof, and antibodies thereto, along with compounds identified as having binding affinity to IL-B30, should be useful as reagents for teaching techniques of molecular biology, immunology, or physiology. Appropriate kits may be prepared with the reagents, e.g., in practical laboratory exercises in production or use of proteins, antibodies, cloning methods, histology, etc.

The reagents will also be useful in the treatment of conditions associated with abnormal physiology or development, including inflammatory conditions. They may be useful in vitro tests for presence or absence of interacting components, which may correlate with success of particular treatment strategies. In particular, modulation of physiology of.various, e.g., hematopoietic or lymphoid, cells will be achieved by appropriate methods for treatment using the compositions provided herein. See, e.g., Thomson (1994; ed.) *The Cytokine Handbook* (2d ed.) Academic Press, San Diego; Metcalf and Nicola (1995) *The Hematopoietic Colony Stimulating Factors* Cambridge University Press; and Aggarwal and Gutterman (1991) *Human Cytokines* Blackwell Pub.

For example, a disease or disorder associated with abnormal expression or abnormal signaling by an IL-B30 should be a likely target for an agonist or antagonist. The new cytokine should play a role in regulation or development of hematopoietic cells, e.g., lymphoid cells, which affect immunological responses, e.g., inflammation and/or autoimmune disorders. Alternatively, it may affect vascular physiology or development, or neuronal effects.

In particular, the cytokine should mediate, in various contexts, cytokine synthesis by the cells, proliferation, etc. Antagonists of IL-B30, such as mutein variants of a naturally occurring form of IL-B30 or blocking antibodies, may provide a selective and powerful way to block immune responses, e.g., in situations as inflammatory or autoimmune responses. See also Samter, et al. (eds.) *Immunological Diseases* vols. 1 and 2, Little, Brown and Co.

In addition, certain combination compositions would be useful, e.g., with other modulators of inflammation. Such other molecules may include steroids, other versions of IL-6 and/or G-CSF, including species variants, or viral homologs, and their respective antagonists.

Various abnormal conditions are known in each of the cell types shown to produce IL-B30 MRNA by Northern blot analysis. See Berkow (ed.) *The Merck Manual of Diagnosis and Therapy*, Merck & Co., Rahway, N.J.; Thorn, et al. *Harrison's Principles of Internal Medicine*, McGraw-Hill, N.Y.; and Weatherall, et al. (eds.) *Oxford Textbook of Medicine*, Oxford University Press, Oxford. Many other medical conditions and diseases involve activation by macrophages or monocytes, and many of these will be responsive to treatment by an agonist or antagonist provided herein. See, e.g., Stites and Terr (eds.; 1991) *Basic and Clinical Immunology* Appleton and Lange, Norwalk, Conn.; and Samter, et al. (eds.) *Immunological Diseases* Little, Brown and Co. These problems should be susceptible to prevention or treatment using compositions provided herein. The pancreatic islet localization suggests a possible relevance to diabetes.

IL-B30, antagonists, antibodies, etc., can be purified and then administered to a patient, veterinary or human. These reagents can be combined for therapeutic use with additional active or inert ingredients, e.g., in conventional pharmaceutically acceptable carriers or diluents, e.g., immunogenic adjuvants, along with physiologically innocuous stabilizers, excipients, or preservatives. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using IL-B30 or fragments thereof can be performed to identify compounds having binding affinity to or other relevant biological effects on IL-B30 functions, including isolation of associated components. Subsequent biological assays can then be utilized to determine if the compound has intrinsic stimulating activity and is therefore a blocker or antagonist in that it blocks the activity of the cytokine. Likewise, a compound having intrinsic stimulating activity can activate the signal pathway and is thus an agonist in that it simulates the activity of IL-B30. This invention further contemplates the therapeutic use of blocking antibodies to IL-B30 as antagonists and of stimulatory antibodies as agonists. This approach should be particularly useful with other IL-B30 species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck.& Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fm (femtomolar), with an appropriate carrier. Slow release formulations, or a slow release apparatus will often be utilized for continuous or long term administration. See, e.g., Langer (1990) *Science* 249:1527–1533.

IL-B30, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, topical, or parenteral (including subcutaneous, intramuscular, intravenous and intradermal) administration. The formulations may conveniently be presented in unit dosage form and may be prepared by any methods well known in the art of pharmacy. See, e.g., Gilman, et. al. (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; Avis, et al. (eds. 1993) *Pharmaceutical Dosaae Forms: Parenteral Medications*, Dekker, N.Y.; Lieberman, et al. (eds. 1990) *Pharmaceutical Dosage Forms: Tablets*, Dekker, N.Y.; and Lieberman, et al. (eds. 1990) *Pharmaceutical Dosage Forms: Disperse Systems*, Dekker, N.Y. The therapy of this invention may be combined with or used in association with other agents, e.g., other cytokines, including IL-6 or G-CSF, or their respective antagonists.

Both naturally occurring and recombinant forms of the IL-B30s of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate. The development of suitable assays can be greatly facilitated by the availability of large amounts of purified, soluble IL-B30 as provided by this invention.

Other methods can be used to determine the critical residues in IL-B30-IL-B30 receptor interactions. Mutational analysis can be performed, e.g., see Somoza, et al. (1993) *J. Exptl. Med.* 178:549–558, to determine specific residues critical in the interaction and/or signaling. PHD (Rost and Sander (1994) *Proteins* 19:55–72) and DSC (King and Sternberg (1996) *Protein Sci.* 5:2298–2310) can provide secondary structure predictions of α-helix (H), β-strand (E), or coil (L). Helices A and D are most important in receptor interaction, with the. D helix the more important region. Helix A would run in the human from about pro(7) to his(27), while helix D would run from about trp(135) to gly(162). Surface exposed residues would affect receptor binding, while embedded residues would affect general structure. Predicted residues of particular importance would likely correspond to arg(146), ser(147), gln(149), ala(150), ala(153), val(154), ala(156), arg(157), ala(160), and his (161).

For example, antagonists can normally be found once the antigen has been structurally defined, e.g., by tertiary structure data. Testing of potential interacting analogs is now possible upon the development of highly automated assay methods using a purified IL-B30. In particular, new agonists and antagonists will be discovered by using screening techniques described herein. Of particular importance are compounds found to have a combined binding affinity for a spectrum of IL-B30 molecules, e.g., compounds which can serve as antagonists for species variants of IL-B30.

One method of drug screening utilizes eukaryotic or prokaryotic host cells which are stably transformed with recombinant DNA molecules expressing an IL-B30. Cells may be isolated which express an IL-B30 in isolation from other molecules. Such cells, either in viable or fixed form, can be used for standard binding partner binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses.

Another technique for drug screening involves an approach which provides high throughput screening for compounds having suitable binding affinity to an IL-B30 and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor; et al. (1991). Then all the pins are reacted with solubilized, unpurified or solubilized, purified IL-B30, and washed. The next step involves detecting bound IL-B30.

Rational drug design may also be based upon structural studies of the molecular shapes of the IL-B30 and other effectors or analogs. Effectors may be other proteins which mediate other functions in response to binding, or other proteins which normally interact with IL-B30, e.g., a receptor. One means for determining which sites interact with specific other proteins is a physical structure determination, e.g., x-ray crystallography or 2 dimensional NMR techniques. These will provide guidance as to which amino acid residues form molecular contact regions, as modeled, e.g., against other cytokine-receptor models. For a detailed description of protein structural determination, see, e.g., Blundell and Johnson (1976) *Protein Crystallography*, Academic Press, N.Y.

IX. Kits

This invention also contemplates use of IL-B30 proteins, fragments thereof, peptides, and their fusion products in a variety of diagnostic kits and methods for detecting the presence of another IL-B30 or binding partner. Typically the kit will have a compartment containing either a defined IL-B30 peptide or gene segment or a reagent which recognizes one or the other, e.g., IL-B30 fragments or antibodies.

A kit for determining the binding affinity of a test compound to an IL-B30 would typically comprise a test compound; a labeled compound, for example a binding partner or antibody having known binding affinity for IL-B30; a source of IL-B30 (naturally occurring or recombinant); and a means for separating bound from free labeled compound, such as a solid phase for immobilizing the molecule. Once compounds are screened, those having suitable binding affinity to the antigen can be evaluated in suitable biological assays, as are well known in the art, to determine whether they act as agonists or antagonists to the IL-B30 signaling pathway. The availability of recombinant IL-B30 polypeptides also provide well defined standards for calibrating such assays.

A preferred kit for determining the concentration of, e.g., an IL-B30 in a sample would typically comprise a labeled compound, e.g., binding partner or antibody, having known binding affinity for the antigen, a source of cytokine (naturally occurring or recombinant) and a means for separating the bound from free labeled compound, e.g., a solid phase for immobilizing the IL-B30. Compartments containing reagents, and instructions, will normally be provided.

Antibodies, including antigen binding fragments, specific for the IL-B30 or fragments are useful in diagnostic applications to detect the presence of elevated levels of IL-B30 and/or its fragments. Such diagnostic assays can employ lysates, live cells, fixed cells, immunofluorescence, cell cultures, body fluids, and further can involve the detection of antigens related to the antigen in serum, or the like. Diagnostic assays may be homogeneous (without a separation step between free reagent and antigen-binding partner complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. See, e.g., Van Vunakis, et al. (1980) *Meth Enzymol.* 70:1–525; Harlow and Lane (1980) *Antibodies: A Laboratory Manual*, CSH Press, N.Y.; and Coligan, et al. (eds. 1993) *Current Protocols in Immunology*, Greene and Wiley, N.Y.

Anti-idiotypic antibodies may have similar use to diagnose presence of antibodies against an IL-B30, as such may be diagnostic of various abnormal states. For example, overproduction of IL-B30 may result in production of various immunological reactions which may be diagnostic of abnormal physiological states, particularly in proliferative cell conditions such as cancer or abnormal activation or differentiation. Moreover, the distribution pattern available provides information that the cytokine is expressed in pancreatic islets, suggesting the possibility that the cytokine may be involved in function of that organ, e.g., in a diabetes relevant medical condition.

Frequently, the reagents for diagnostic assays are supplied in kits, so as to optimize the sensitivity of the assay. For the subject invention, depending upon the nature of the assay, the protocol, and the label, either labeled or unlabeled antibody or binding partner, or labeled IL-B30 is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification or may be modified in a.variety of ways. For example, labeling may be achieved by covalently or non-covalently joining a moiety which directly or indirectly provides a detectable signal. In any of these assays, the binding partner, test compound, IL-B30, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free IL-B30, or alternatively the bound from the free test compound. The IL-B30 can be immobilized on various matrixes followed by washing. Suitable matrixes include plastic such as an ELISA plate, filters, and beads. See, e.g., Coligan, et al. (eds. 1993) *Current Protocols in Immunology*, Vol. 1, Chapter 2, Greene and Wiley, N.Y. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an IL-B30. These sequences can be used as probes for detecting levels of the IL-B30 message in samples from patients suspected of having an abnormal condition, e.g., inflammatory or autoimmune. Since the cytokine may be a marker or mediator for activation, it may be useful to determine the numbers of activated cells to determine, e.g., when additional therapy may be called for, e.g., in a preventative fashion before the effects become and progress to significance. The preparation of both RNA and DNA nucleotide sequences, the labeling of the sequences, and the preferred size of the sequences has received ample description and discussion in the literature. See, e.g., Langer-Safer, et al. (1982) *Proc. Nat'l. Acad. Sci.* 79:4381–4385; Caskey (1987) *Science* 236:962–967; and Wilchek et al. (1988) *Anal. Biochem.* 171:1–32.

Diagnostic kits which also test for the qualitative or quantitative expression of other molecules are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97. Other kits may be used to evaluate other cell subsets.

X. Isolating a IL-B30 Receptor

Having isolated a ligand of a specific ligand-receptor interaction, methods exist for isolating the receptor. See, Gearing, et al. (1989) *EMBO J.* 8:3667–3676. For example, means to label the IL-B30 cytokine without interfering with the binding to its receptor can be determined. For example, an affinity label can be fused to either the amino- or carboxyl-terminus of the ligand. Such label may be a FLAG epitope tag, or, e.g., an Ig or Fc domain. An expression library can be screened for specific binding of the cytokine, e.g., by cell sorting, or other screening to detect subpopulations which express such a binding component. See, e.g., Ho, et al. (1993) *Proc. Nat'l Acad. Sci. USA* 90:11267–11271; and Liu, et al. (1994) *J. Immunol.* 152:1821–29. Alternatively, a panning method may be used. See, e.g., Seed and Aruffo (1987) *Proc. Nat'l Acad. Sci. USA* 84:3365–3369.

Protein cross-linking techniques with label can be applied to isolate binding partners of the IL-B30 cytokine. This would allow identification of proteins which specifically interact with the cytokine, e.g., in a ligand-receptor like manner.

Early experiments will be performed to determine whether the known IL-6 or G-CSF receptor components are involved in response(s) to IL-B30. It is also quite possible that these functional receptor complexes may share many or all components with an IL-B30 receptor complex, either a specific receptor subunit or an accessory receptor subunit.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

EXAMPLES

I. General Methods

Many of the standard methods below are described or referenced, e.g., in Maniatis, et al. (1982) *Molecular Clonina. A Laboratory Manual* Cold Spring Harbor Laboratory, Cold Spring Harbor Press, NY; Sambrook, et al. (1989) *Molecular Clonina: A Laboratory Manual* (2d ed.) Vols. 1–3, CSH Press, N.Y.; Ausubel, et al., Biology Greene Publishing Associates, Brooklyn, N.Y.; or Ausubel, et al. (1987 and Supplements) *Current Protocols in Molecular Biology* Wiley/Greene, N.Y.; Innis, et al. (eds. 1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology* vol. 182, and other volumes in this series; Coligan, et al. (1995 and supplements) *Current Protocols in Protein Science* John Wiley and Sons, New York, N.Y.; P. Matsudaira (ed. 1993) *A Practical Guide to Protein and Peptide Purification for Microsequencing*, Academic Press, San Diego, Calif.; and manufacturer's literature on use of protein purification products, e.g., Pharmacia, Piscataway, NJ, or Bio-Rad, Richmond, Calif. Combination with recombinant techniques allow fusion to appropriate segments (epitope tags), e.g., to a FLAG sequence or an equivalent which can be fused, e.g., via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *OIAexpress: The Hiah Level Expression & Protein Purification System* QUIAGEN, Inc., Chatsworth, Calif.

Standard immunological techniques are described, e.g., in Hertzenberg, et al. (eds. 1996) *Weir's Handbook of Experimental Immunolocry* vols. 1–4, Blackwell Science; Coligan (1991) *Current Protocols in Immunology* Wiley/Greene, N.Y.; and *Methods in Enzymology* vols. 70, 73, 74, 84, 92, 93, 108, 116, 121, 132, 150, 162, and 163. Cytokine assays are described, e.g., in Thomson (ed. 1994) *The Cytokine Handbook* (2d ed.) Academic Press, San Diego; Metcalf and Nicola (1995). *The Hematopoietic Colony Stimulatina Factors* Cambridge University Press; and Aggarwal and Gutterman (1991) *Human Cytokines* Blackwell Pub.

Assays for vascular biological activities are well known in the art. They will cover angiogenic and angiostatic activities in tumor, or other tissues, e.g., arterial smooth muscle proliferation (see, e.g., Koyoma, et al. (1996) *Cell* 87:1069–1078), monocyte adhesion to vascular epithelium (see McEvoy, et al. (1997) *J. Exp. Med.* 185:2069–2077), etc. See also Ross (1993) *Nature* 362:801–809; Rekhter and Gordon (1995) *Am. J. Pathol.* 147:668–677; Thyberg, et al. (1990) *Atherosclerosis* 10:96614 990; and Gumbiner (1996) *Cell* 84:345–357.

Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Cloning of Human IL-B30

The sequence of the gene is provided in Table 1. The sequence is derived from a cDNA library made from melanocyte, fetal heart; and pregnant uterus. It is also found from a cDNA library sequence derived from a pancreatic islet. These sequences allow preparation of PCR primers, or probes, to determine cellular distribution of the gene. The sequences allow isolation of genomic DNA which encode the message.

Using the probe or PCR primers, various tissues or cell types are probed to determine cellular distribution. PCR products are cloned using, e.g., a TA cloning kit (Invitrogen). The resulting cDNA plasmids are sequenced from both termini on an automated sequencer (Applied Biosystems).

III. Cellular Expression of IL-B30

An appropriate probe or primers specific for cDNA encoding primate IL-B30 are prepared. Typically, the probe is labeled, e.g., by random priming. The expression is probably in the cell types described, and perhaps also in pancreatic islets. Southern Analysis: DNA (5 $\mu$g) from a primary amplified cDNA library was digested with appropriate restriction enzymes to release the inserts, run on a 1% agarose gel and transferred to a nylon membrane (Schleicher and Schuell, Keene, N.H.).

Samples for human mRNA isolation include: peripheral blood mononuclear cells (monocytes, T cells, NK cells, granulocytes, B cells), resting (T100); peripheral blood mononuclear cells, activated with anti-CD3 for 2, 6, 12 h pooled (T1010); T cell, TH0 clone Mot 72, resting (T102); T cell, TH0 clone Mot 72, activated with anti-CD28 and anti-CD3 for 3, 6, 12 h pooled (T103); T cell, TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (T109); T cell, TH2 clone HY935, resting (T110); T cell, TH2 clone HY935, activated with anti-CD28 and anti-CD3 for 2, 7, 12 h pooled (T111); T cell tumor lines Jurkat and Hut78, resting (T117); T cell clones, pooled AD130.2, Tc783.12, Tc783.13, Tc783.58, Tc782.69, resting (T118); T cell random γδ T cell clones, resting (T119); CD28-T cell clone; Splenocytes, resting (B100); Splenocytes, activated with anti-CD40 and IL-4 (B1010); B cell EBV lines pooled WT49, RSB, JY, CVIR, 721.221, RM3, HSY, resting (B102); B cell line JY, activated with PMA and ionomycin for 1, 6 h pooled (B103); NK 20 clones pooled, resting (K100); NK 20 clones pooled, activated with PMA and ionomycin for 6 h (K101); NKL clone, derived from peripheral blood of LGL leukemia patient, IL-2 treated (K106); hematopoietic precursor line TF1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFNγ, anti-IL-10 for 1, 2, 6, 12, 24 h pooled (M102); elutriated monocytes, activated with LPS, IFNγ, IL-10 for 1, 2, 6, 12, 24 h pooled (M103); elutriated monocytes, activated with LPS, IFNγ, anti-IL-10 for 4, 16 h pooled (M106); elutriated monocytes, activated with LPS, IFNγ, IL-10 for 4, 16 h pooled (M107); elutriated monocytes, activated LPS for 1 h (M108); elutriated monocytes, activated LPS for 6 h (M109); DC 70% CD1a+, from CD34+ GM-CSF, TNFα 12 days, resting (D101); DC 70% CD1a+, from CD34+ GM-CSF, TNFα 12 days, activated with PMA and ionomycin for 1 hr (D102); DC 70% CD1a+, from CD34+ GM-CSF, TNFα 12 days, activated with PMA and ionomycin for 6 hr (D103); DC 95% CD1a+, from CD34+ GM-CSF, TNFα 12 days FACS sorted, activated with PMA and ionomycin for 1, 6 h pooled (D104); DC 95% CD14+, ex CD34+ GM-CSF, TNFα 12 days FACS sorted, activated with PMA and ionomycin 1, 6 hr pooled (D105); DC CD1a+ CD86+, from CD34+ GM-CSF, TNFα 12 days FACS sorted, activated with PMA and ionomycin for 1, 6 h pooled (D106); DC from monocytes GM-CSF, IL-4 5 days, resting (D107); DC from monocytes GM-CSF, IL-4 5 days, resting (D108); DC from monocytes GM-CSF, IL-4 5 days, activated LPS 4, 16 h pooled (D109); DC from monocytes GM-CSF, IL-4 5 days, activated TNFα, monocyte supe for 4, 16 h pooled (D110); epithelial cells, unstimulated; epithelial cells, IL-1β activated; lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102). Expression of IL-B30 transcript was very high in elutriated monocytes, activated with LPS, IFNγ, anti-IL-10 for 4, 16 h pooled (M106); elutriated monocytes, activated with LPS, IFNγ, anti-IL-10 for 1, 2, 6, 12, 24 h pooled (M102); elutriated monocytes, activated LPS for 6 h (M109); and elutriated monocytes, activated LPS for 1 h (M108). Expression was high in DC 95% CD1a+, from CD34+GM-CSF, TNFα 12 days FACS. sorted, activated with PMA and ionomycin for 1, 6 h pooled (D104); and NK 20 clones pooled, activated with PMA and ionomycin for 6 h (K101). Lesser expression was detected in DC 70% CD1a+, from CD34+ GM-CSF, TNFα 12 days, activated with PMA and ionomycin for 6 hr (D103); DC 70% CD1a+, from CD34+ GM-CSF, TNFα 12 days, activated with PMA and ionomycin for 1 hr (D102); T cell, TH1 clone HY06, anergic treated with specific peptide for 2, 6, 12 h pooled (T109); peripheral blood mononuclear cells, activated with anti-CD3 for 2, 6, 12 h pooled (T101); T cell, TH0 clone Mot 72, activated with anti-CD28 and anti-CD3 for 3, 6, 12 h pooled (T103); Splenocytes, activated with anti-CD40 and IL-4 (B101); T cell, TH0 clone Mot 72, anergic treated with specific peptide for 2, 7, 12 h pooled (T104); Splenocytes, resting (B100); T cell, TH1 clone HY06, activated with anti-CD28 and anti-CD3 for 3, 6, 12 h pooled (T108); epithelial cells, IL-1β activated; elutriated monocytes, activated with LPS, IFNγ, IL-10 for 4, 16 h pooled (M107); and B cell line JY, activated with PMA and ionomycin for 1, 6 h pooled (B103). Detectable expression was observed in DC from monocytes GM-CSF, IL-4 5 days, activated LPS 4, 16 h pooled (D109); T cell, TH0 clone Mot 72, resting (T102); peripheral blood mononuclear cells (monocytes, T cells, NK cells, granulocytes, B cells), resting (T100);T cells CD4+ CD45RO− T cells polarized 27 days in anti-CD28, IL-4, and anti IFN-γ, TH2 polarized, activated with anti-CD3 and anti-CD28 4 h (T116); T cell clones, pooled AD130.2, Tc783.12, Tc783.13, Tc783.58, Tc782.69, resting (T118); U937 premonocytic line, resting (M100); hematopoietic precursor line TF1, activated with PMA and ionomycin for 1, 6 h pooled (C100); T cell, TH2 clone HY935, activated with anti-CD28 and anti-CD3 for 2, 7, 12 h pooled (T111); DC CD1a+ CD86+, from CD34+ GM-CSF, TNFα 12 days FACS sorted, activated with PMA and ionomycin for 1, 6 h pooled (D106); elutriated monocytes, activated with LPS, IFNγ, IL-10 for 1, 2, 6, 12, 24 h pooled (M103); DC from monocytes GM-CSF, IL-4 5 days, activated TNFα, monocyte supe for 4, 16 h pooled. (D110); DC from monocytes GM-CSF, IL-4 5 days, resting (D108); U937 premonocytic line, activated with PMA and ionomycin for 1, 6 h pooled (M101); T cell random γδ T cell clones, resting (T119); and T cell, TH1 clone HY06, activated with anti-CD28 and anti-CD3 for 3, 6, 12 h pooled (T108). No signal was detected in the other samples.

In summary, the distribution shows IL-B30 elevated in activated macrophages, suggesting a role in inflammation; activated Th1 cells, suggesting a regulation or effector role in T helper subsets, particularly Th1 immune responses; and activated dendritic cells, suggesting a role in antigen presentation or germinal center T or B cell interactions with DC.

Samples for mouse mRNA isolation include: resting mouse fibroblastic L cell line (C200); Braf:ER (Braf fusion to estrogen receptor) transfected cells, control (C201); Mel14+ naive T cells from spleen, resting (T209); Mel14+ naive T cells from spleen, stimulated with IFNγ, IL-12, and anti IL-4 to polarize to TH1 cells, exposed to IFNγ and IL-4 for 6, 12, 24 h, pooled (T210); Mel14+naive T cells from spleen, stimulated with IL-4 and anti IFNγ to polarize to Th2 cells, exposed to IL-4 and anti IFNγ for 6, 13, 24 h, pooled (T211); T cells, TH1 polarized (Mel14 bright, CD4+ cells from spleen, polarized for 7 days with IFN-γ and anti IL-4; T200); T cells, TH2 polarized (Mell4 bright, CD4+ cells from spleen, polarized for 7 days with IL-4 and anti-IFN-γ; T201); T cells, highly TH1 polarized 3× from transgenic Balb/C (see Openshaw, et al. (1995) *J. Exp. Med.* 182:1357–1367; activated with anti-CD3 for 2, 6, 24 h pooled; T202); T cells, highly TH2 polarized 3× from transgenic Balb/C (activated with anti-CD3 for 2, 6, 24 h pooled (T203); T cells, highly TH1 polarized 3× from transgenic C57 bl/6 (activated with anti-CD3 for 2, 6, 24 h pooled; T212); T cells, highly TH2 polarized 3× from transgenic C57 bl/6 (activated with anti-CD3 for 2, 6, 24 h pooled; T213); T cells, highly TH1 polarized (naive CD4+ T cells from transgenic Balb/C, polarized 3× with IFNγ, IL-12, and anti-IL-4; stimulated with IGIF, IL-12, and anti IL-4 for 6, 12, 24 h, pooled); CD44− CD25+ pre T cells, sorted from thymus (T204); TH1 T cell clone D1.1, resting for 3 weeks after last stimulation with antigen (T205); TH1 T cell clone D1.1, 10 μg/ml ConA stimulated 15 h (T206); TH2 T cell clone CDC35, resting for 3 weeks after last stimulation with antigen (T207); TH2 T cell clone CDC35, 10 μg/ml ConA stimulated 15 h (T208); unstimulated B cell line CH12 (B201); unstimulated mature B cell leukemia cell line A20 (B200); unstimulated large B cells from spleen (B202); B cells from total spleen, LPS activated (B203); metrizamide enriched dendritic cells from spleen, resting (D200); dendritic cells from bone marrow, resting (D201); unstimulated bone marrow derived dendritic cells depleted with anti B220, anti CD3, and anti Class II, cultured in GM-CSF and IL-4 (D202); bone marrow derived dendritic cells depleted with anti B220, anti CD3, and anti Class II, cultured in GM-CSF and IL-4, stimulated with anti CD40 for 1, 5 d, pooled (D203); monocyte cell line RAW 264.7 activated with LPS 4 h (M200); bone-marrow macrophages derived with GM and M-CSF (M201); bone-marrow macrophages derived with GM-CSF, stimulated with LPS, IFNγ, and IL-10 for 24 h (M205); bone-marrow macrophages derived with GM-CSF, stimulated with LPS, IFNγ, and anti IL-10 for 24 h (M206); peritoneal macrophages (M207); macrophage cell line J774, resting (M202); macrophage cell line J774 +LPS +anti-IL-10 at 0.5, 1, 3, 6, 12 h pooled (M203); macrophage cell line J774 +LPS +IL-10 at 0.5, 1, 3, 5, 12 h pooled (M204); unstimulated mast cell lines MC-9 and MCP-12. (M208); immortalized endothelial cell line derived from brain microvascular endothelial cells, unstimulated (E200); immortalized endothelial cell line derived from brain microvascular endothelial cells, stimulated overnight with TNFα (E201); immortalized endothelial cell line derived from brain microvascular endothelial cells, stimulated overnight with TNFα (E202); immortalized endothelial cell line derived from brain microvascular endothelial cells, stimulated overnight with TNFα and IL-10 (E203); total aorta from wt C57 bl/6 mouse; total aorta from 5 month ApoE KO mouse (X207); total aorta from 12 month ApoE KO mouse (X207); wt thymus (O214); total thymus, rag-1 (O208); total kidney, rag-1 (O209); total kidney, NZ B/W mouse; and total heart, rag-1 (O202). High signal was detected in the monocyte cell line RAW 264.7 activated with LPS 4 h (M200); T cells, highly TH1 polarized 3× from transgenic C57 bl/6 (activated with anti-CD3 for 2, 6, 24 h pooled; T212); and T cells, highly TH1 polarized (naive CD4+ T cells from transgenic Balb/C, polarized 3× with IFNγ, IL-12, and anti-IL-4; stimulated with IGIF, IL-12, and anti IL-4 for 6, 12, 24 h, pooled). Detectable signals were detected in T cells, highly TH1 polarized 3× from transgenic Balb/C (see Openshaw, et al. (1995) *J. Exp. Med.* 182:1357–1367; activated with anti-CD3 for 2, 6, 24 h pooled; T202); T cells, TH2 polarized (Mel14 bright, CD4+ cells from spleen, polarized for 7 days with IL-4 and anti-IFN-γ; T201); T cells, TH1 polarized (Mel14 bright, CD4+ cells from spleen, polarized for 7 days with IFN-γ and anti IL-4; T200); macrophage cell line J774 + LPS + anti-IL-10 at 0.5, 1, 3, 6, 12 h pooled (M203); macrophage cell line J774, resting (M202); macrophage cell line J774 + LPS + IL-10 at 0.5, 1, 3, 5, 12 h pooled (M204); immortalized endothelial cell line derived from brain microvascular endothelial cells, stimulated overnight with TNFA (E201); and bone-marrow macrophages derived with GM-CSF, stimulated with LPS, IFNγ, and anti IL-10 for 24 h (M206). Other samples showed no signal. The expression in the RAW 264.7 mouse monocyte cell line suggests a natural source for protein.

IV. Chromosome mapping of IL-B30

An isolated cDNA encoding the IL-B30 is used. Chromosome mapping is a standard technique. See, e.g., BIOS Laboratories (New Haven, Conn.) and methods for using a mouse somatic cell hybrid panel with PCR. Circumstantial evidence suggests that the mouse gene is localized on chromosome 10.

V. Purification of IL-B30 Protein

Multiple transfected cell lines are screened for one which expresses the cytokine at a high level compared with other cells. Various cell lines are screened and selected for their favorable properties in handling. Natural IL-B30 can be isolated from natural sources, or by expression from a transformed cell using an appropriate expression vector. Purification of the expressed protein is achieved by standard procedures, or may be combined with engineered means for effective purification at high efficiency from cell lysates or supernatants. FLAG or $His_6$ segments can be used for such purification features. Alternatively, affinity chromatography may be used with specific antibodies, see below.

Protein is produced in *coli*, insect cell, or mammalian expression systems, as desired.

VI. Isolation of Homologous IL-B30 Genes

The IL-B30 cDNA, or other species counterpart sequence, can be used as a hybridization probe to screen a library from a desired source, e.g., a primate cell cDNA library. Many different species can be screened both for stringency necessary for easy hybridization, and for presence using a probe. Appropriate hybridization conditions will be used to select for clones exhibiting specificity of cross hybridization.

Screening by hybridization using degenerate probes based upon the peptide sequences will also allow isolation of appropriate clones. Alternatively, use of appropriate primers for PCR screening will yield enrichment of appropriate nucleic acid clones.

Similar methods are applicable to isolate either species, polymorphic, or allelic variants. Species variants are isolated using cross-species hybridization techniques based upon isolation of a full length isolate or fragment from one species as a probe.

Alternatively, antibodies raised against human IL-B30 will be used to screen for cells which express cross-reactive proteins from an appropriate, e.g., cDNA library. The purified protein or defined peptides are useful for generating antibodies by standard methods, as described above. Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. The resulting antibodies are used for screening, purification, or diagnosis, as described.

VII. Preparation of Antibodies Specific for IL-B30

Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. Polyclonal serum, or hybridomas may be prepared. In appropriate situations, the binding reagent is either labeled as described above, e.g., fluorescence or otherwise, or immobilized to a substrate for panning methods. Immunoselection and related techniques are available to prepare selective reagents, as desired.

VIII. Evaluation of Breadth of Biological Functions

Biological activities of IL-B30 were tested based on the sequence and structural homology between IL-B30 and IL-6 and G-CSF. Initially, assays that had shown biological activities of IL-6 or G-CSF are examined.

A. Effects on Proliferation of Cells

The effect on proliferation of various cell types are evaluated with various concentrations of cytokine. A dose response analysis is performed, in combinations with the related cytokines IL-6, G-CSF, etc.

B. Effects on the Expression of Cell Surface Molecules on Human Monocytes

Monocytes are purified by negative selection from peripheral blood mononuclear cells of normal healthy donors. Briefly, $3 \times 10^8$ ficoll banded mononuclear cells are incubated on ice with a cocktail of monoclonal antibodies (Becton-Dickinson; Mountain View, Calif.) consisting, e.g., of 200 μl of αCD2 (Leu-5A), 200 μl of αCD3 (Leu-4), 100 μl of αCD8 (Leu 2a), 100 μl of αCD19 (Leu-12 ), 100 μl of αCD20 (Leu-16), 100 μl of αCD56 (Leu-19), 100 μl of αCD67 (IOM 67; Immunotech, Westbrook, Me.), and anti-glycophorin antibody (10F7MN, ATCC, Rockville, Md.). Antibody bound cells are washed and then incubated with sheep anti-mouse IgG coupled magnetic beads (Dynal, Oslo, Norway) at a bead to cell ratio of 20:1. Antibody bound cells are separated from monocytes by application of a magnetic field. Subsequently, human monocytes are cultured in Yssel's medium (Gemini Bioproducts, Calabasas, Calif.) containing 1% human AB serum in the absence or presence of IL-B30, IL-6, G-CSF or combinations.

Analyses of the expression of cell surface molecules can be performed by direct immunofluorescence. For example, $2 \times 10^5$ purified human monocytes are incubated in phosphate buffered saline (PBS) containing 1% human serum on ice for 20 minutes. Cells are pelleted at 200×g. Cells are resuspended in 20 ml PE or FITC labeled mAb. Following an additional 20 minute incubation on ice, cells are washed in PBS containing 1% human serum followed by two washes in PBS alone. Cells are fixed in PBS containing 1% paraformaldehyde and analyzed on FACScan flow cytometer (Becton Dickinson; Mountain View, Calif.). Exemplary mAbs are used, e.g.: CD11b (anti-mac1), CD11c (a gp150/95), CD14 (Leu-M3), CD54 (Leu 54), CD80 (anti-BB1/B7), HLA-DR (L243) from Becton-Dickinson and CD86 (FUN 1; Pharmingen), CD64 (32.2; Medarex), CD40 (mAb89; Schering-Plough France).

C. Effects of IL-B30 on Cytokine Production by Human Monocytes

Human monocytes are isolated as described and cultured in Yssel's medium (Gemini Bioproducts, Calabasas, Calif.) containing 1% human AB serum in the absence or presence of IL-B30 (1/100 dilution baculovirus expressed material). In addition, monocytes are stimulated with LPS (*E. coli* 0127:B8 Difco) in the absence or presence of IL-B30 and the concentration of cytokines (IL-1β, IL-6, TNFα, GM-CSF, and IL-10) in the cell culture supernatant determined by ELISA.

For intracytoplasmic staining for cytokines, monocytes are cultured (1 million/ml) in Yssel's medium in the absence or presence of IL-B30 and LPS (*E. coli* 0127:B8 Difco) and 10 mg/ml Brefeldin A (Epicentre technologies Madison Wiss.) for 12 hrs. Cells are washed in PBS and incubated in 2% formaldehyde/PBS solution for 20 minutes at RT. Subsequently cells are washed, resuspended in permeabilization buffer (0.5% saponin (Sigma) in PBS/BSA (0.5%)/Azide (1 mM)) and incubated for 20 minutes at RT. Cells ($2 \times 10^5$) are centrifuged and resuspended in 20 ml directly conjugated anti-cytokine mAbs diluted 1:10 in permeabilization buffer for 20 minutes at RT. The following antibodies can be used: IL-1α-PE (364-3B3-14); IL-6-PE (MQ2-13A5); TNFα-PE (MAb11); GM-CSF-PE (BVD2-21C11); and IL-12-PE (C11.5.14; Pharmingen San Diego, Calif.). Subsequently, cells are washed twice in permeabilization buffer and once in PBS/BSA/Azide and analyzed on FACScan flow cytometer (Becton Dickinson; Mountain View, Calif.).

D. Effects of IL-B30 on Proliferation of Human Peripheral Blood Mononuclear Cells (PBMC).

Total PBMC are isolated from buffy coats of normal healthy donors by centrifugation through ficoll-hypaque as described (Boyum, et al.). PBMC are cultured in 200 μl Yssel's medium (Gemini Bioproducts, Calabasas, Calif.) containing 1% human AB serum in 96 well plates (Falcon, Becton-Dickinson, N.J.) in the absence or presence of IL-B30. Cells are cultured in medium alone or in combination with 100 U/ml IL-2 (R&D Systems) for 120 hours. 3H-Thymidine (0.1 mCi) is added during the last six hours of culture and 3H-Thymidine incorporation determined by liquid scintillation counting.

The native, recombinant, and fusion proteins would be tested for agonist and antagonist activity in many other biological assay systems, e.g., on T-cells, B-cells, NK, macrophages, dendritic cells, hematopoietic progenitors, etc. Because of the IL-6 and G-CSF structural relationship, assays related to those activities should be analyzed IL-B30 is evaluated for agonist or antagonist activity on transfected cells expressing IL-6 or G-CSF receptor and controls. See, e.g., Ho, et al. (1993) *Proc. Nat'l Acad. Sci. USA* 90, 11267–11271; Ho, et al. (1995) *Mol. Cell. Biol.* 15:5043–5053; and Liu, et al. (1994). *J. Immunol.* 152:1821–1829.

IL-B30 is evaluated for effect in macrophage/dendritic cell activation and antigen presentation assays, T cell cytokine production and proliferation in response to antigen or allogeneic stimulus. See, e.g., de Waal Malefyt et al. (1991) *J. Exp. Med.* 174:1209–1220; de Waal Malefyt et al. (1991) *J. Exp. Med.* 174:915–924; Fiorentino, et al. (1991) *J. Immunol.* 147, 3815–3822; Fiorentino, et al. (1991) *J. Immunol.* 146:3444–3451; and Groux, et al. (1996) *J. Exp. Med.* 184:19–29.

IL-B30 will also be evaluated for effects on NK cell stimulation. Assays may be based, e.g., on Hsu, et al. (1992) *Internat. Immunol.* 4:563–569; and Schwarz, et al. (1994) *J. Immunother.* 16:95–104.

B cell growth and differentiation effects will be analyzed, e.g., by the methodology described, e.g., in Defrance, et al. (1992). *J. Exp. Med.* 175:671–682; Rousset, et al. (1992) *Proc. Nat'l Acad. Sci. USA* 89:1890–1893; including IgG2 and IgA2 switch factor assays. Note that, unlike COS7 supernatants, NIH3T3 and COP supernatants apparently do not interfere with human B cell assays.

IX. Generation and Analysis of Genetically Altered Animals

Transgenic mice can be generated by standard methods. Such animals are useful to determine the effects of deletion of the gene, in specific tissues, or completely throughout the organism. Such may provide interesting insight into development of the animal or particular tissues in various stages. Moreover, the effect on various responses to biological stress can be evaluated. See, e.g., Hogan, et al. (1995) *Maniulating the Mouse Embryo: A Laboratory Manual* (2d ed.) Cold Spring Harbor Laboratory Press.

A transgenic mouse has been generated, and while the animal seems to survive birth, it fails to thrive, and typically dies within a few weeks. The construct is based upon an actin promoter with a CMV enhancer, which should lead to broad and high expression. The mice, like IL-6 transgenic mice, are runted. Moreover, they exhibit a bloated abdomen, inflammation of the stomach and intestines, infiltration of cells into the liver, and typically die before day 50. These mice do not breed. A second subset of the transgenic mice have a less severe phenotype, and attempts to breed them are taking place.

The genomic structure for the mouse IL-B30 has been determined. A strategy for the production of IL-B30 knock-out mice has been developed, and constructs have been started.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A binding compound comprising an antibody binding site which specifically binds to residues 1–168 of SEQ ID NO:2.

2. The binding compound of claim 1, wherein said antibody binding site is specifically immunoreactive with a polypeptide of SEQ ID NO:2.

3. A method of making the binding composition of claim 1, comprising administering to an animal:
   a) a substantially pure and isolated polypeptide comprising residues 1–168 of SEQ ID NO:2;
   b) a substantially pure and isolated polypeptide comprising residues 1–175 of SEQ ID NO:4; or
   c) a substantially pure or isolated polypeptide comprising SEQ ID NO:5, whereby said animal produces said binding compound.

4. The binding compound of claim 1, wherein said antibody binding site is raised against a purified or recombiantly produced protein which comprises residues 1–168 of SEQ ID NO:2.

5. The binding compound of claim 4, wherein said binding compound is an antibody molecule.

6. The binding compound of claim 4, wherein said binding compound is a polyclonal antiserum.

7. The binding compound of claim 4, wherein said binding compound is detectably labeled.

8. The binding compound of claim 4, wherein said binding compound is in a sterile buffered composition.

* * * * *

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 570 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..567

(ix) FEATURE:
      (A) NAME/KEY: mat_peptide
      (B) LOCATION: 64..567

(xi) SEQUENCE DESCRIPTION: SEQ ID NO: 1:

```
ATG CTG GGG AGC AGA GCT GTA ATG CTG CTG TTG CTG CTG CCC TGG ACA        48
Met Leu Gly Ser Arg Ala Val Met Leu Leu Leu Leu Leu Pro Trp Thr
-21 -20                 -15                 -10

GCT CAG GGC AGA GCT GTG CCT GGG GGC AGC AGC CCT GCC TGG ACT CAG        96
Ala Gln Gly Arg Ala Val Pro Gly Gly Ser Ser Pro Ala Trp Thr Gln
 -5              1               5                  10

TGC CAG CAG CTT TCA CAG AAG CTC TGC ACA CTG GCC TGG AGT GCA CAT       144
Cys Gln Gln Leu Ser Gln Lys Leu Cys Thr Leu Ala Trp Ser Ala His
             15                  20                  25

CCA CTA GTG GGA CAC ATG GAT CTA AGA GAA GAG GGA GAT GAA GAG ACT       192
Pro Leu Val Gly His Met Asp Leu Arg Glu Glu Gly Asp Glu Glu Thr
         30                  35                  40

ACA AAT GAT GTT CCC CAT ATC CAG TGT GGA GAT GGC TGT GAC CCC CAA       240
Thr Asn Asp Val Pro His Ile Gln Cys Gly Asp Gly Cys Asp Pro Gln
     45                  50                  55

GGA CTC AGG GAC AAC AGT CAG TTC TGC TTG CAA AGG ATC CAC CAG GGT       288
Gly Leu Arg Asp Asn Ser Gln Phe Cys Leu Gln Arg Ile His Gln Gly
 60                  65                  70                  75

CTG ATT TTT TAT GAG AAG CTG CTA GGA TCG GAT ATT TTC ACA GGG GAG       336
Leu Ile Phe Tyr Glu Lys Leu Leu Gly Ser Asp Ile Phe Thr Gly Glu
                 80                  85                  90

CCT TCT CTG CTC CCT GAT AGC CCT GTG GCG CAG CTT CAT GCC TCC CTA       384
Pro Ser Leu Leu Pro Asp Ser Pro Val Ala Gln Leu His Ala Ser Leu
             95                 100                 105

CTG GGC CTC AGC CAA CTC CTG CAG CCT GAG GGT CAC CAC TGG GAG ACT       432
Leu Gly Leu Ser Gln Leu Leu Gln Pro Glu Gly His His Trp Glu Thr
         110                 115                 120

CAG CAG ATT CCA AGC CTC AGT CCC AGC CAG CCA TGG CAG CGT CTC CTT       480
Gln Gln Ile Pro Ser Leu Ser Pro Ser Gln Pro Trp Gln Arg Leu Leu
     125                 130                 135

CTC CGC TTC AAA ATC CTT CGC AGC CTC CAG GCC TTT GTG GCT GTA GCC       528
Leu Arg Phe Lys Ile Leu Arg Ser Leu Gln Ala Phe Val Ala Val Ala
140                 145                 150                 155

GCC CGG GTC TTT GCC CAT GGA GCA GCA ACC CTG AGT CCC TAA               570
Ala Arg Val Phe Ala His Gly Ala Ala Thr Leu Ser Pro
                 160                 165
```

(2) INFORMATION FOR SEQ ID NO: 2:

(i) SEQUENCE CHARACTERISTICS:
    (A) LENGTH: 189 amino acids
    (B) TYPE: amino acid
    (D) TOPOLOGY: linear (ii) MOLECULE TYPE: protein (xi) SEQUENCE DESCRIPTION: SEQ ID NO: 2:

```
Met Leu Gly Ser Arg Ala Val Met Leu Leu Leu Leu Pro Trp Thr
-21 -20             -15                 -10

Ala Gln Gly Arg Ala Val Pro Gly Gly Ser Ser Pro Ala Trp Thr Gln
-5              1               5                   10

Cys Gln Gln Leu Ser Gln Lys Leu Cys Thr Leu Ala Trp Ser Ala His
            15              20                  25

Pro Leu Val Gly His Met Asp Leu Arg Glu Glu Gly Asp Glu Glu Thr
            30              35                  40

Thr Asn Asp Val Pro His Ile Gln Cys Gly Asp Gly Cys Asp Pro Gln
            45              50              55

Gly Leu Arg Asp Asn Ser Gln Phe Cys Leu Gln Arg Ile His Gln Gly
60              65              70              75

Leu Ile Phe Tyr Glu Lys Leu Leu Gly Ser Asp Ile Phe Thr Gly Glu
            80              85              90

Pro Ser Leu Leu Pro Asp Ser Pro Val Ala Gln Leu His Ala Ser Leu
            95              100             105

Leu Gly Leu Ser Gln Leu Leu Gln Pro Glu Gly His His Trp Glu Thr
            110             115             120

Gln Gln Ile Pro Ser Leu Ser Pro Ser Gln Pro Trp Gln Arg Leu Leu
            125             130             135

Leu Arg Phe Lys Ile Leu Arg Ser Leu Gln Ala Phe Val Ala Val Ala
140             145             150             155

Ala Arg Val Phe Ala His Gly Ala Ala Thr Leu Ser Pro
                160             165
```

(2) INFORMATION FOR SEQ ID NO: 3:

(i) SEQUENCE CHARACTERISTICS:
    (A) LENGTH: 1203 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 113..700

(ix) FEATURE:
    (A) NAME/KEY: mat_peptide
    (B) LOCATION: 176..700

(xi) SEQUENCE DESCRIPTION: SEQ ID NO: 3:

```
CGCTTAGAAG TCGGACTACA GAGTTAGACT CAGAACCAAA GGAGGTGGAT AGGGGGTCCA      60

CAGGCCTGGT GCAGATCACA GAGCCAGCCA GATCTGAGAA GCAGGGAACA AG ATG        115
                                                          Met
                                                          -21

CTG GAT TGC AGA GCA GTA ATA ATG CTA TGG CTG TTG CCC TGG GTC ACT      163
Leu Asp Cys Arg Ala Val Ile Met Leu Trp Leu Leu Pro Trp Val Thr
-20             -15              -10                  -5

CAG GGC CTG GCT GTG CCT AGG AGT AGC AGT CCT GAC TGG GCT CAG TGC      211
Gln Gly Leu Ala Val Pro Arg Ser Ser Ser Pro Asp Trp Ala Gln Cys
            1               5                   10
```

```
CAG CAG CTC TCT CGG AAT CTC TGC ATG CTA GCC TGG AAC GCA CAT GCA       259
Gln Gln Leu Ser Arg Asn Leu Cys Met Leu Ala Trp Asn Ala His Ala
        15                  20                  25

CCA GCG GGA CAT ATG AAT CTA CTA AGA GAA GAA GAG GAT GAA GAG ACT       307
Pro Ala Gly His Met Asn Leu Leu Arg Glu Glu Glu Asp Glu Glu Thr
        30                  35                  40

AAA AAT AAT GTG CCC CGT ATC CAG TGT GAA GAT GGT TGT GAC CCA CAA       355
Lys Asn Asn Val Pro Arg Ile Gln Cys Glu Asp Gly Cys Asp Pro Gln
 45                  50                  55                  60

GGA CTC AAG GAC AAC AGC CAG TTC TGC TTG CAA AGG ATC CGC CAA GGT       403
Gly Leu Lys Asp Asn Ser Gln Phe Cys Leu Gln Arg Ile Arg Gln Gly
                65                  70                  75

CTG GCT TTT TAT AAG CAC CTG CTT GAC TCT GAC ATC TTC AAA GGG GAG       451
Leu Ala Phe Tyr Lys His Leu Leu Asp Ser Asp Ile Phe Lys Gly Glu
            80                  85                  90

CCT GCT CTA CTC CCT GAT AGC CCC ATG GAG CAA CTT CAC ACC TCC CTA       499
Pro Ala Leu Leu Pro Asp Ser Pro Met Glu Gln Leu His Thr Ser Leu
        95                  100                 105

CTA GGA CTC AGC CAA CTC CTC CAG CCA GAG GAT CAC CCC CGG GAG ACC       547
Leu Gly Leu Ser Gln Leu Leu Gln Pro Glu Asp His Pro Arg Glu Thr
    110                 115                 120

CAA CAG ATG CCC AGC CTG AGT TCT AGT CAG CAG TGG CAG CGC CCC CTT       595
Gln Gln Met Pro Ser Leu Ser Ser Ser Gln Gln Trp Gln Arg Pro Leu
125                 130                 135                 140

CTC CGT TCC AAG ATC CTT CGA AGC CTC CAG GCC TTT TTG GCC ATA GCT       643
Leu Arg Ser Lys Ile Leu Arg Ser Leu Gln Ala Phe Leu Ala Ile Ala
                145                 150                 155

GCC CGG GTC TTT GCC CAC GGA GCA GCA ACT CTG ACT GAG CCC TTA GTG       691
Ala Arg Val Phe Ala His Gly Ala Ala Thr Leu Thr Glu Pro Leu Val
            160                 165                 170

CCA ACA GCT TAAGGATGCC CAGGTTCCCA TGGCTACCAT GATAAGACTA               740
Pro Thr Ala
        175

ATCTATCAGC CCAGACATCT ACCAGTTAAT TAACCCATTA GGACTTGTGC TGTTCTTGTT     800

TCGTTTGTTT TGCGTGAAGG GCAAGGACAC CATTATTAAA GAGAAAGAA ACAAACCCCA      860

GAGCAGGCAG CTGGCTAGAG AAAGGAGCTG GAGAAGAAGA ATAAAGTCTC GAGCCCTTGG     920

CCTTGGAAGC GGGCAAGCAG CTGCGTGGCC TGAGGGGAAG GGGGCGGTGG CATCGAGAAA     980

CTGTGAGAAA ACCCAGAGCA TCAGAAAAAG TGAGCCCAGG CTTTGGCCAT TATCTGTAAG    1040

AAAAACAAGA AAAGGGGAAC ATTATACTTT CCTGGGTGGC TCAGGGAAAT GTGCAGATGC    1100

ACAGTACTCC AGACAGCAGC TCTGTACCTG CCTGCTCTGT CCCTCAGTTC TAACAGAATC    1160

TAGTCACTAA GAACTAACAG GACTACCAAT ACGAACTGAC AAA                      1203
```

(2) INFORMATION FOR SEQ ID NO: 4:

(i) SEQUENCE CHARACTERISTICS:
        (A) LENGTH: 196 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Leu Asp Cys Arg Ala Val Ile Met Leu Trp Leu Leu Pro Trp Val
-21 -20                 -15                 -10

Thr Gln Gly Leu Ala Val Pro Arg Ser Ser Ser Pro Asp Trp Ala Gln
 -5                   1                   5                  10
```

-continued

Cys Gln Gln Leu Ser Arg Asn Leu Cys Met Leu Ala Trp Asn Ala His
              15                  20                  25

Ala Pro Ala Gly His Met Asn Leu Leu Arg Glu Glu Asp Glu Glu
         30                  35                  40

Thr Lys Asn Asn Val Pro Arg Ile Gln Cys Glu Asp Gly Cys Asp Pro
         45                  50                  55

Gln Gly Leu Lys Asp Asn Ser Gln Phe Cys Leu Gln Arg Ile Arg Gln
 60              65                  70                  75

Gly Leu Ala Phe Tyr Lys His Leu Leu Asp Ser Asp Ile Phe Lys Gly
                 80                  85                  90

Glu Pro Ala Leu Leu Pro Asp Ser Pro Met Glu Gln Leu His Thr Ser
             95                 100                 105

Leu Leu Gly Leu Ser Gln Leu Leu Gln Pro Glu Asp His Pro Arg Glu
            110                 115                 120

Thr Gln Gln Met Pro Ser Leu Ser Ser Gln Gln Trp Gln Arg Pro
            125                 130                 135

Leu Leu Arg Ser Lys Ile Leu Arg Ser Leu Gln Ala Phe Leu Ala Ile
140                 145                 150                 155

Ala Ala Arg Val Phe Ala His Gly Ala Ala Thr Leu Thr Glu Pro Leu
                160                 165                 170

Val Pro Thr Ala
        175

(2) INFORMATION FOR SEQ ID NO: 5:

(i) SEQUENCE CHARACTERISTICS:
        (A) LENGTH: 102 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 5:

Ser Cys Leu Gln Arg Ile His Gln Gly Leu Val Phe Tyr Glu Lys Leu
 1               5                  10                  15

Leu Gly Ser Asp Ile Phe Thr Gly Glu Pro Ser Leu His Pro Asp Gly
             20                  25                  30

Ser Val Gly Gln Leu His Ala Ser Leu Leu Gly Leu Arg Gln Leu Leu
             35                  40                  45

Gln Pro Glu Gly His His Trp Glu Thr Glu Gln Thr Pro Ser Pro Ser
 50                  55                  60

Pro Ser Gln Pro Trp Gln Arg Leu Leu Leu Arg Leu Lys Ile Leu Arg
 65                  70                  75                  80

Ser Leu Gln Ala Phe Val Ala Val Ala Ala Arg Val Phe Ala His Gly
                 85                  90                  95

Ala Ala Thr Leu Ser Gln
            100

(2) INFORMATION FOR SEQ ID NO: 6:

(i) SEQUENCE CHARACTERISTICS:
        (A) LENGTH: 174 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 6:

-continued

```
Thr Pro Leu Gly Pro Ala Arg Ser Leu Pro Gln Ser Phe Leu Leu Lys
 1               5                  10                  15

Cys Leu Glu Gln Val Arg Lys Ile Gln Ala Asp Gly Ala Glu Leu Gln
            20                  25                  30

Glu Arg Leu Cys Ala Ala His Lys Leu Cys His Pro Glu Glu Leu Met
            35                  40                  45

Leu Leu Arg His Ser Leu Gly Ile Pro Gln Ala Pro Leu Ser Ser Cys
        50                  55                  60

Ser Ser Gln Ser Leu Gln Leu Arg Gly Cys Leu Asn Gln Leu His Gly
 65                  70                  75                  80

Gly Leu Phe Leu Tyr Gln Gly Leu Leu Gln Ala Leu Ala Gly Ile Ser
                85                  90                  95

Pro Glu Leu Ala Pro Thr Leu Asp Thr Leu Gln Leu Asp Val Thr Asp
                100                 105                 110

Phe Ala Thr Asn Ile Trp Leu Gln Met Glu Asp Leu Gly Ala Ala Pro
            115                 120                 125

Ala Val Gln Pro Thr Gln Gly Ala Met Pro Thr Phe Thr Ser Ala Phe
        130                 135                 140

Gln Arg Arg Ala Gly Gly Val Leu Val Ala Ser Gln Leu His Arg Phe
145                 150                 155                 160

Leu Glu Leu Ala Tyr Arg Gly Leu Arg Tyr Leu Ala Glu Pro
                165                 170
```

(2) INFORMATION FOR SEQ ID NO: 7:

(i) SEQUENCE CHARACTERISTICS:
        (A) LENGTH: 174 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 7:

```
Thr Pro Leu Gly Pro Thr Ser Ser Leu Pro Gln Ser Phe Leu Leu Lys
 1               5                  10                  15

Cys Leu Glu Gln Val Arg Lys Val Gln Ala Asp Gly Thr Ala Leu Gln
            20                  25                  30

Glu Arg Leu Cys Ala Ala His Lys Leu Cys His Pro Glu Glu Leu Val
            35                  40                  45

Leu Leu Gly His Ala Leu Gly Ile Pro Gln Ala Pro Leu Ser Ser Cys
        50                  55                  60

Ser Ser Gln Ala Leu Gln Leu Thr Gly Cys Leu Arg Gln Leu His Ser
 65                  70                  75                  80

Gly Leu Phe Leu Tyr Gln Gly Leu Leu Gln Ala Leu Ala Gly Ile Ser
                85                  90                  95

Pro Glu Leu Ala Pro Thr Leu Asp Met Leu Gln Leu Asp Ile Thr Asp
                100                 105                 110

Phe Ala Ile Asn Ile Trp Gln Gln Met Glu Asp Val Gly Met Ala Pro
            115                 120                 125

Ala Val Pro Pro Thr Gln Gly Thr Met Pro Thr Phe Thr Ser Ala Phe
        130                 135                 140

Gln Arg Arg Ala Gly Gly Thr Leu Val Ala Ser Asn Leu Gln Ser Phe
145                 150                 155                 160

Leu Glu Val Ala Tyr Arg Ala Leu Arg His Phe Thr Lys Pro
                165                 170
```

(2) INFORMATION FOR SEQ ID NO: 8:

(i) SEQUENCE CHARACTERISTICS:
        (A) LENGTH: 177 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 8:

```
Thr Pro Leu Gly Pro Ala Ser Ser Leu Pro Gln Ser Phe Leu Leu Lys
 1               5                  10                  15

Cys Leu Glu Gln Val Arg Lys Ile Gln Gly Asp Gly Ala Ala Leu Gln
            20                  25                  30

Glu Lys Leu Val Ser Glu Cys Ala Thr Tyr Lys Leu Cys His Pro Glu
        35                  40                  45

Glu Leu Val Leu Leu Gly His Ser Leu Gly Ile Pro Trp Ala Pro Leu
    50                  55                  60

Ser Ser Cys Pro Ser Gln Ala Leu Gln Leu Ala Gly Cys Leu Ser Gln
65                  70                  75                  80

Leu His Ser Gly Leu Met Ala Pro Ala Leu Gln Pro Thr Gln Gly Ala
                85                  90                  95

Met Pro Ala Phe Ala Ser Ala Phe Gln Arg Arg Ala Gly Gly Val Leu
            100                 105                 110

Val Ala Ser His Leu Gln Ser Phe Leu Glu Val Ser Tyr Arg Val Leu
        115                 120                 125

Arg His Leu Ala Gln Phe Leu Tyr Gln Gly Leu Leu Gln Ala Leu Glu
    130                 135                 140

Gly Ile Ser Pro Glu Leu Gly Pro Thr Leu Asp Thr Leu Gln Leu Asp
145                 150                 155                 160

Val Ala Asp Phe Ala Thr Thr Ile Trp Gln Gln Met Glu Glu Leu Gly
                165                 170                 175

Pro
```

(2) INFORMATION FOR SEQ ID NO: 9:

(i) SEQUENCE CHARACTERISTICS:
        (A) LENGTH: 178 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 9:

```
Val Pro Leu Val Thr Val Ser Ala Leu Pro Pro Ser Leu Pro Leu Pro
 1               5                  10                  15

Arg Ser Phe Leu Leu Lys Ser Leu Glu Gln Val Arg Lys Ile Gln Ala
            20                  25                  30

Ser Gly Ser Val Leu Leu Glu Gln Leu Cys Ala Thr Tyr Lys Leu Cys
        35                  40                  45

His Pro Glu Glu Leu Val Leu Leu Gly His Ser Leu Gly Ile Pro Lys
    50                  55                  60

Ala Ser Leu Ser Gly Cys Ser Ser Gln Ala Leu Gln Gln Thr Gln Cys
65                  70                  75                  80

Leu Ser Gln Leu His Ser Gly Leu Cys Leu Tyr Gln Gly Leu Leu Gln
                85                  90                  95
```

```
Ala Leu Ser Gly Ile Ser Pro Ala Leu Ala Pro Thr Leu Asp Leu Leu
            100                 105                 110

Gln Leu Asp Val Ala Asn Phe Ala Thr Thr Ile Trp Gln Gln Met Glu
            115                 120                 125

Asn Leu Gly Val Ala Pro Thr Val Gln Pro Thr Gln Ser Ala Met Pro
            130                 135                 140

Ala Phe Thr Ser Ala Phe Gln Arg Arg Ala Gly Gly Val Leu Ala Ile
145                 150                 155                 160

Ser Tyr Leu Gln Gly Phe Leu Glu Thr Ala Arg Leu Ala Leu His His
                165                 170                 175

Leu Ala (2) INFORMATION FOR SEQ ID NO: 10:

(i) SEQUENCE CHARACTERISTICS:
        (A) LENGTH: 186 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 10:

Ala Phe Pro Thr Pro Gly Pro Leu Gly Gly Asp Ser Lys Asp Asp Ala
1               5                   10                  15

Thr Ser Asn Arg Pro Pro Leu Thr Ser Ala Asp Lys Met Glu Asp Phe
            20                  25                  30

Ile Lys Phe Ile Leu Gly Lys Ile Ser Ala Leu Arg Asn Glu Met Cys
            35                  40                  45

Asp Lys Tyr Asn Lys Cys Glu Asp Ser Lys Glu Val Leu Ala Glu Asn
50                  55                  60

Asn Leu Asn Leu Pro Lys Leu Ala Glu Lys Asp Arg Cys Phe Gln Ser
65                  70                  75                  80

Arg Phe Asn Gln Glu Thr Cys Leu Thr Arg Ile Thr Thr Gly Leu Gln
            85                  90                  95

Glu Phe Gln Ile His Leu Lys Tyr Leu Glu Ser Asn Tyr Glu Gly Asn
            100                 105                 110

Lys Asp Asn Ala His Ser Val Tyr Ile Ser Thr Lys His Leu Leu Gln
            115                 120                 125

Thr Leu Arg Pro Met Asn Gln Ile Glu Val Thr Thr Pro Asp Pro Thr
            130                 135                 140

Thr Asp Ala Ser Leu Gln Ala Leu Phe Lys Ser Gln Asp Lys Trp Leu
145                 150                 155                 160

Lys His Thr Thr Ile His Leu Ile Leu Arg Arg Leu Glu Asp Phe Leu
                165                 170                 175

Gln Phe Ser Leu Arg Ala Ile Arg Ile Met
            180                 185

(2) INFORMATION FOR SEQ ID NO: 11:

(i) SEQUENCE CHARACTERISTICS:
        (A) LENGTH: 183 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 11:
```

```
Ala Phe Pro Thr Pro Gly Pro Leu Gly Gly Asp Ala Thr Ser Asn Arg
1               5                   10                  15

Leu Pro Leu Thr Pro Ala Asp Lys Met Glu Glu Leu Ile Lys Tyr Ile
            20                  25                  30

Leu Gly Lys Ile Ser Ala Leu Lys Lys Glu Met Cys Asp Asn Tyr Asn
            35                  40                  45

Lys Cys Glu Asp Ser Lys Glu Ala Leu Ala Glu Asn Asn Leu Asn Leu
        50                  55                  60

Pro Lys Leu Ala Glu Lys Asp Gly Cys Phe Gln Ser Gly Phe Asn Gln
65                  70                  75                  80

Glu Thr Cys Leu Thr Arg Ile Thr Thr Gly Leu Gln Glu Phe Gln Ile
                85                  90                  95

Tyr Leu Lys Phe Leu Gln Asp Lys Tyr Glu Gly Asp Lys Glu Asn Ala
                100                 105                 110

Lys Ser Val Tyr Thr Ser Thr Asn Val Leu Leu Gln Met Leu Lys Arg
            115                 120                 125

Lys Gly Lys Asn Gln Asp Glu Val Thr Ile Pro Val Pro Thr Val Glu
            130                 135                 140

Val Gly Leu Gln Leu Ser Cys Ser His Arg Arg Val Ala Glu Ala His
145                 150                 155                 160

Asn Asn His Leu Thr Leu Arg Arg Leu Glu Asp Phe Leu Gln Leu Arg
                165                 170                 175

Leu Arg Ala Val Arg Ile Met
                180

(2) INFORMATION FOR SEQ ID NO: 12:

(i) SEQUENCE CHARACTERISTICS:
        (A) LENGTH: 188 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

Ala Phe Pro Ala Pro Val Pro Gly Glu Asp Ser Lys Asp Val Ala
1               5                   10                  15

Ala Pro His Arg Gln Pro Leu Thr Ser Ser Glu Arg Ile Asp Lys Gln
            20                  25                  30

Ile Arg Tyr Ile Leu Asp Gly Ile Ser Ala Leu Arg Lys Glu Thr Cys
            35                  40                  45

Asn Lys Ser Asn Met Cys Glu Ser Ser Lys Glu Ala Leu Ala Glu Asn
        50                  55                  60

Asn Leu Asn Leu Pro Lys Met Ala Glu Lys Asp Gly Cys Phe Gln Ser
65                  70                  75                  80

Gly Phe Asn Glu Glu Thr Cys Leu Val Lys Ile Ile Thr Gly Leu Leu
                85                  90                  95

Glu Phe Glu Val Tyr Leu Glu Tyr Leu Gln Asn Arg Phe Glu Ser Ser
                100                 105                 110

Glu Glu Gln Ala Arg Ala Val Gln Met Ser Thr Lys Val Leu Ile Gln
            115                 120                 125

Phe Leu Gln Lys Lys Ala Lys Asn Leu Asp Ala Ile Thr Thr Pro Asp
            130                 135                 140

Pro Thr Thr Asn Ala Ser Leu Leu Thr Lys Leu Gln Ala Gln Asn Gln
145                 150                 155                 160
```

```
Trp Leu Gln Asp Met Thr Thr His Leu Ile Leu Arg Ser Phe Lys Glu
                165                 170                 175
Phe Leu Gln Ser Ser Leu Arg Ala Leu Arg Gln Met
            180                 185

(2) INFORMATION FOR SEQ ID NO: 13:

(i) SEQUENCE CHARACTERISTICS:
        (A) LENGTH: 184 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 13:

Ala Phe Pro Thr Pro Gly Pro Leu Gly Glu Asp Phe Lys Asn Asp Thr
1               5                   10                  15
Thr Pro Ser Arg Leu Leu Leu Thr Thr Pro Glu Lys Thr Glu Ala Leu
            20                  25                  30
Ile Lys His Ile Val Asp Lys Ile Ser Ala Ile Arg Lys Glu Ile Cys
        35                  40                  45
Glu Lys Asn Asp Glu Cys Glu Asn Ser Lys Glu Thr Leu Ala Glu Asn
50                  55                  60
Lys Leu Lys Leu Pro Lys Met Glu Glu Lys Asp Gly Cys Phe Gln Ser
65                  70                  75                  80
Gly Phe Asn Gln Ala Ile Cys Leu Ile Lys Thr Thr Ala Gly Leu Leu
                85                  90                  95
Glu Tyr Gln Ile Tyr Leu Asp Phe Leu Gln Asn Glu Phe Glu Gly Asn
            100                 105                 110
Gln Glu Thr Val Met Glu Leu Gln Ser Ser Ile Arg Thr Leu Ile Gln
        115                 120                 125
Ile Leu Lys Glu Lys Ile Ala Gly Leu Ile Thr Thr Pro Ala Thr His
130                 135                 140
Thr Asp Met Leu Glu Lys Met Gln Ser Ser Asn Glu Trp Val Lys Asn
145                 150                 155                 160
Ala Lys Val Ile Ile Ile Leu Arg Ser Leu Glu Asn Phe Leu Gln Phe
                165                 170                 175
Ser Leu Arg Ala Ile Arg Met Lys
            180

(2) INFORMATION FOR SEQ ID NO: 14:

(i) SEQUENCE CHARACTERISTICS:
        (A) LENGTH: 188 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 14:

Ala Phe Pro Thr Ser Gln Val Arg Arg Gly Asp Phe Thr Glu Asp Thr
1               5                   10                  15
Thr Pro Asn Arg Pro Val Tyr Thr Thr Ser Gln Val Gly Gly Leu Ile
            20                  25                  30
Thr His Val Leu Trp Glu Ile Val Glu Met Arg Lys Glu Leu Cys Asn
        35                  40                  45
Gly Asn Ser Asp Cys Met Asn Asn Asp Asp Ala Leu Ala Glu Asn Asn
```

```
            50                  55                  60
Leu Lys Leu Pro Glu Ile Gln Arg Asn Asp Gly Cys Tyr Gln Thr Gly
 65                  70                  75                  80

Tyr Asn Gln Glu Ile Cys Leu Leu Lys Ile Ser Ser Gly Leu Leu Glu
                     85                  90                  95

Tyr His Ser Tyr Leu Glu Tyr Met Lys Asn Asn Leu Lys Asp Asn Lys
                    100                 105                 110

Lys Asp Lys Ala Arg Val Leu Gln Arg Asp Thr Glu Thr Leu Ile His
                115                 120                 125

Ile Phe Asn Gln Glu Val Lys Asp Leu His Lys Ile Val Leu Pro Thr
                130                 135                 140

Pro Ile Ser Asn Ala Leu Leu Thr Asp Lys Leu Glu Ser Gln Lys Glu
145                 150                 155                 160

Trp Leu Arg Thr Lys Thr Ile Gln Phe Ile Leu Lys Ser Leu Glu Glu
                165                 170                 175

Phe Leu Lys Val Thr Leu Arg Ser Thr Arg Gln Thr
                180                 185

(2) INFORMATION FOR SEQ ID NO: 15:

(i) SEQUENCE CHARACTERISTICS:
        (A) LENGTH: 178 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 15:

Ala Pro Leu Ala Glu Leu Ser Gly Asp His Asp Phe Gln Leu Phe Leu
 1                   5                  10                  15

His Lys Asn Leu Glu Phe Thr Arg Lys Ile Arg Gly Asp Val Ala Ala
                 20                  25                  30

Leu Gln Arg Ala Val Cys Asp Thr Phe Gln Leu Cys Thr Glu Glu Glu
                 35                  40                  45

Leu Gln Leu Val Gln Pro Asp Pro His Leu Val Gln Ala Pro Leu Asp
 50                  55                  60

Gln Cys His Lys Arg Gly Phe Gln Ala Gly Val Cys Phe Thr Gln Ile
 65                  70                  75                  80

Arg Ala Gly Leu His Ala Tyr His Asp Ser Leu Gly Ala Val Leu Arg
                 85                  90                  95

Leu Leu Pro Asn His Thr Thr Leu Val Glu Thr Leu Gln Leu Asp Ala
                100                 105                 110

Ala Asn Leu Ser Ser Asn Ile Gln Gln Gln Met Glu Asp Leu Gly Leu
                115                 120                 125

Asp Thr Val Thr Leu Pro Ala Glu Gln Arg Ser Pro Pro Thr Phe
                130                 135                 140

Ser Gly Pro Phe Gln Gln Gln Val Gly Gly Phe Phe Ile Leu Ala Asn
145                 150                 155                 160

Phe Gln Arg Phe Leu Glu Thr Ala Tyr Arg Ala Leu Arg His Leu Ala
                165                 170                 175

Arg Leu (2) INFORMATION FOR SEQ ID NO: 16:

(i) SEQUENCE CHARACTERISTICS:
        (A) LENGTH: 185 amino acids
```

(B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 16:

Thr Arg Gly Lys Leu Pro Asp Ala Pro Glu Phe Glu Lys Asp Leu Leu
1               5                   10                  15

Ile Gln Arg Leu Asn Trp Met Leu Trp Val Ile Asp Glu Cys Phe Arg
            20                  25                  30

Asp Leu Cys Tyr Arg Thr Gly Ile Cys Lys Gly Ile Leu Glu Pro Ala
        35                  40                  45

Ala Ile Phe His Leu Lys Leu Pro Ala Ile Asn Asp Thr Asp His Cys
    50                  55                  60

Gly Leu Ile Gly Phe Asn Glu Thr Ser Cys Leu Lys Lys Leu Ala Asp
65                  70                  75                  80

Gly Phe Phe Glu Phe Glu Val Leu Phe Lys Phe Leu Thr Thr Glu Phe
                85                  90                  95

Gly Lys Ser Val Ile Asn Val Asp Val Met Glu Leu Leu Thr Lys Thr
                100                 105                 110

Leu Gly Trp Asp Ile Gln Glu Glu Leu Asn Lys Leu Thr Lys Thr His
            115                 120                 125

Tyr Ser Pro Pro Lys Phe Asp Arg Gly Leu Leu Gly Arg Leu Gln Gly
        130                 135                 140

Leu Lys Tyr Trp Val Arg His Phe Ala Ser Phe Tyr Val Leu Ser Ala
145                 150                 155                 160

Met Glu Lys Phe Ala Gly Gln Ala Val Arg Val Leu Asp Ser Ile Pro
                165                 170                 175

Asp Val Thr Pro Asp Val His Asp Lys
            180                 185